(12) United States Patent
Johnson et al.

(10) Patent No.: US 7,807,720 B2
(45) Date of Patent: Oct. 5, 2010

(54) HYDROXAMIC ACID DERIVATIVES OF 3-PHENYL PROPIONIC ACIDS USEFUL AS THERAPEUTIC AGENTS FOR TREATING ANTHRAX POISONING

(75) Inventors: Alan T. Johnson, Kaneohe, HI (US); Guan-Sheng Jiao, Honolulu, HI (US)

(73) Assignee: PanThera Biopharma, LLC, Aiea, HI (US)

( * ) Notice: Subject to any disclaimer, the term of this patent is extended or adjusted under 35 U.S.C. 154(b) by 205 days.

(21) Appl. No.: 12/011,888

(22) Filed: Jan. 30, 2008

(65) Prior Publication Data

US 2008/0188566 A1 Aug. 7, 2008

Related U.S. Application Data

(60) Provisional application No. 60/898,965, filed on Feb. 1, 2007.

(51) Int. Cl.
*A61K 31/165* (2006.01)
*C07C 239/00* (2006.01)

(52) U.S. Cl. ..................... 514/617; 564/161
(58) Field of Classification Search ................. 514/617; 564/161
See application file for complete search history.

(56) References Cited

U.S. PATENT DOCUMENTS

| 4,751,296 | A | 6/1988 | Miller |
| 6,420,427 | B1 | 7/2002 | Takahashi |
| 2005/0148629 | A1 | 7/2005 | Xiong |

FOREIGN PATENT DOCUMENTS

| WO | WO 97/24117 | 7/1997 |
| WO | WO 03/101382 | 12/2003 |
| WO | WO 2005/027856 A2 | 3/2005 |

OTHER PUBLICATIONS

Takahashi et al., 1999, CAS: 130:311803.*
Gasparini et al., 1980, CAS: 92:66434.*
Venkatesan et al., 1998, CAS: 129:230641.*
U.S. Appl. No. 12/011,790, filed Jan. 30, 2008, Johnson.
U.S. Appl. No. 12/011,847, filed Jan. 30, 2008, Johnson.
Xiong et al. The discovery of a potent and selective lethal factor inhibitor for adjunct therapy of anthrax infection. Bioorg. Med. Chem. Lett. 2006; 16, 964-8. Compound 40.
Summers et al. Hydroxamic Acid Inhibitors of 5-Lipoxygenase: Quantitative Structure-Activity Relationships. J. Med. Chem. 1990, 33, 992-998. See Compounds 82, 94-96, p. 995.
Sparks et al.. Type 2 Intramolecular N-Acylnitroso Diels-Alder Reaction " . . . ". J. Org. Chem. 2004, 69, 3025-3035. Compound 4a to 4c. p. 3026.
Rajendra et al. Intramolecular Electrophilic Additins to Olefins in Organic Syntheses. Stereoselective Synthesis " . . . ". J. Org. Chem. 1987, 52, 4471-4477. See Compound 4b.
Couturier, M.; et al. 5,5-Dimethyl-1,4,2-dioxazoles as Versitle Aprotic Hydroxamic Acid Protecting Groups. J. Org. Chem. 2002, 67, 4833-4838. See Compound 1e and 1f, p. 4835.
Xianfeng, et al., Design and Evaluation of Hydroxamate Derivatives as Metal-Mediated Inhibitors of a Protein . . . , J. Med. Chem., 2006, 49, 7532-7539. See p. 7534.
Caplow, et al., Discrete Effects of the Acylamino Proton in a Chymotrypsin Substrate . . . , Journal of the American Chemical Society, 94:18, Sep. 6, 1972, pp. 6508-6512.

* cited by examiner

*Primary Examiner*—Rei-tsang Shiao
(74) *Attorney, Agent, or Firm*—Gabor L. Szekeres

(57) ABSTRACT

Compounds having the formula wherein the symbols have the meaning described in the specification are hydroxamic acid derivatives of 3-phenyl-propionic acid and capable of inhibiting the lethal effects of infection by anthrax bacteria and are useful in the treatment of poisoning by anthrax.

19 Claims, No Drawings

HYDROXAMIC ACID DERIVATIVES OF 3-PHENYL PROPIONIC ACIDS USEFUL AS THERAPEUTIC AGENTS FOR TREATING ANTHRAX POISONING

CLAIM OF PRIORITY

The present application claims the priority of U.S. provisional application Ser. No. 60/898,965 filed on Feb. 1, 2007.

STATEMENT REGARDING FEDERALLY SPONSORED RESEARCH OR DEVELOPMENT

This invention was made with government support under Grant no. R44AI052587 awarded by the National Institutes of Health. The US government has certain rights in the invention.

BACKGROUND OF THE INVENTION

1. Field of the Invention

The present invention is directed to compounds useful for treatment of poisoning by *bacillus anthracis* (anthrax infection or poisoning). More particularly, the invention is directed to compounds capable of inhibiting the lethal effects of infection by anthrax bacteria and are useful in the treatment of poisoning by anthrax. The compounds of the invention are hydroxamic acid derivatives of 3-phenyl-propionic acid.

2. Background Art

Anthrax is a disease caused by infection of mammals, including humans, by *bacillus anthracis*. Spores of these bacteria can enter the mammalian, including human body, through skin abrasions, the digestive system or inhalation. Whereas anthrax poisoning in humans through skin abrasion or the digestive system can often be treated with antibiotics, anthrax poisoning in humans by ingestion of aerosol usually results in death of the infected individual.

Relatively recently, devices have been made which incorporate *bacillus anthracis* or its spores and are capable of releasing the bacteria or its spores in aerosol form. This "weaponized" form of anthrax can serve as a "weapon of mass destruction" in biological warfare and is feared in the Western World for its potential use by terrorists against civilian populations.

For all these reasons a serious effort has been made in the fields of medical and related biological research to elucidate the mode and agent of poisoning by *bacillus anthracis* and efforts have been made to synthesize compounds which act as inhibitors of the lethal toxins and therefore can treat the infection.

The following scientific publications describe or relate to the manner of infection by the bacteria and to elucidation of the toxic factors and their mode of action in the mammalian, including human body: Dixon et al. (1999) N. England J. Med. 341. 815-26; Mock et al. Annu. Rev. Microbiol. 55. 647-71; Vitalae et al. (1998) Biochem. Biopphys. Res. Commun. 248, 706-11; Vitalae et al. (2000) Biochem J. 352 Pt 3, 739-45; Duesbery et al. (1998) Science 280. 734-7; Duesbery et al. International Publication No. WO 99/50439; Hammond et al. (1998) Infect. Immun. 66, 2374-8. A summary of these findings is that the toxin, called "lethal factor", released by *bacillus anthraci* is an enzyme that splits an essential peptide needed by mammalian organisms for signal transmission. Thus, inhibitors of this bacterial enzyme are candidates for drugs for treatment of anthrax poisoning.

Published US Patent Application No. 2005/0148629 (Jul. 7, 2005) describes hydroxamic acid compounds which have the general formula shown below where the $R^1$ is aryl, or heteroaryl, or heterocyclic and where R represents a large number of potential substituents, including alkyl, and which can be used in the treatment of anthrax poisoning.

Published International Application WO 2005/027856 (Mar. 31, 2005) describes numerous compounds said to be inhibitors of anthrax lethal factor.

Published International Application WO 97/24117 discloses compounds of the general formula including some examples where the variable p=1, q=0 and m=1. Said compounds are said to be inhibitors of cyclic AMP phosphodiesterase.

Published European Patent Application EP 1 707 560 A1 includes formulas 1 through 10 (pages 1-15) which purport to cover a very large number of compounds of diverging structures, some of which are pertinent to the compounds of the present invention.

The present invention represents a further advance in the field by providing hydroxamic acid derivatives of phenyl-propionic acid which are useful to treat anthrax poisoning.

SUMMARY OF THE INVENTION

The present invention relates to compounds of Formula 1

Formula 1 where
$R^1$ is F, Cl, Br, I, alkyl of 1-3 carbons, alkoxy of 1-3 carbons, thioalkoxy of 1-3 carbons, phenyl, O-phenyl, CN, $CF_3$, $OCF_3$; OH, $NH_2$, $NHC_1$-$C_6$alkyl, $N(C_1$-$C_6$alkyl$)_2$, $CO_2H$ or $CO_2(C_1$-$C_6$ alkyl);
m is an integer having the value of 1 to 3;
$R^2$ is alkyl of 1-9 carbons; $C_1$-$C_6$ alkylphenyl where phenyl is substituted with 0-3 $R^1$ groups, $C_1$-$C_6$ alkylcyclohexyl, $(CH_2)_nOR^3$, $(CH_2)_nNHR^4$, $NR^4C_1$-$C_6$alkyl, $(CH_2)_nCF_3$, $CH_2OCH_2$-phenyl; $(CH_2)_nNH(CH_2)_nR^4$, $(CH_2)_nNR^6R^4$, $(CH_2)_nNR^6(CH_2)_nR^4$, $(CH_2)_nO(CH_2)_nR^4$, $(CH_2)_nOR^4$, CN, phenyl substituted with 0 to 3 R¹ groups, an alkenyl group having 2 to 9 carbons and one double bond, n is an integer having the value of 1 to 8;

R³ is H, alkyl of 1 to 6 carbons, alkylphenyl where the alkylgroup has 1 to 6 carbons and the phenyl is substituted with 0-3 R¹ groups;

R⁴ is H, alkyl of 1 to 10 carbons, $(CH_2)_p$cyclohexyl, C(O)alkyl of 1 to 4 carbons, C(O)alkylphenyl where the alkylgroup has 1 to 4 carbons and the phenyl is substituted with 0-3 R¹ groups or with a 5 to 6 membered heteroayl group having 1 to 2 heteroatoms selected from O, S, and N, or with a 5 to 6 membered heteroaryl group having 1 to 2 heteroatoms selected from O, S and N and condensed with a phenylgroup, said heteroaryl or condensed heteroaryl group itself substituted with 0-3 R¹ groups, or R⁴ is $C(O)(CH_2)_p$COOH, $(CH_2)_p$phenyl where the phenyl is substituted with 0-3 R¹ groups or with a $NO_2$ group, or R⁴ is $C(O)OC_1$-$C_6$alkyl, or R⁴ is $CH(CH_3)$phenyl where the phenyl is substituted with 0-3 R¹ groups, or R⁴ is $C(O)(CH_2)_p$phenyl where the phenyl is substituted with 0-3 R¹ groups, or R⁴ is $C(O)CH(Ph)_2$, C(O)—$CH_2$-(3PhO—)Ph, or R⁴ is a 5 to 6 membered heteroaryl group having 1 to 2 heteroatoms selected from O, S, and N, or a 5 to 6 membered heteroaryl group having 1 to 2 heteroatoms selected from O, S and N and condensed with a phenyl group, said heteroaryl or condensed heteroaryl group itself substituted with 0-3 R¹ groups, or R⁴ is $CH_2$heteroaryl ** $CH_2$heteroaryl condensed with phenyl where the heteroaryl group is 5 or 6 membered and has 1 to 2 heteroatoms selected from O, S said heteroaryl group or condensed heteroaryl itself substituted with 0-3 R¹ groups, or R⁴ is $SO_2$-alkyl of 1 to 6 carbons, $SO_2$-Ph where the phenyl is substituted with 0-3 R¹ groups or with $NO_2$ or with $COOR^5$ group, or R⁴ is C(O)NH-alkylphenyl, or C(O)NH-phenyl where the alkyl group has 1 to 4 carbons and where the phenyl is substituted with 0-3 R¹ groups;

p is an integer having the value of 0 to 4;

R⁵ is alkyl of 1 to 6 carbons or phenyl substituted with 0-3 R¹ groups or with an OPh group;

R⁶ is alkyl of 1 to 6 carbons;

the star indicates an asymmetric carbon, the wavy line represents a bond that can be in the R or in the S configuration, or a pharmaceutically acceptable salt of said compound, with the proviso that compounds selected from the group consisting of compounds identified below with structural formulas

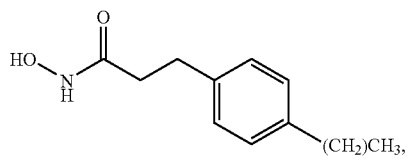

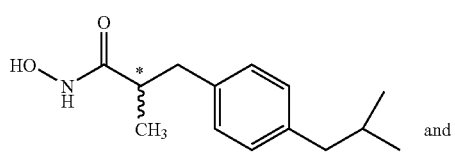
and

-continued

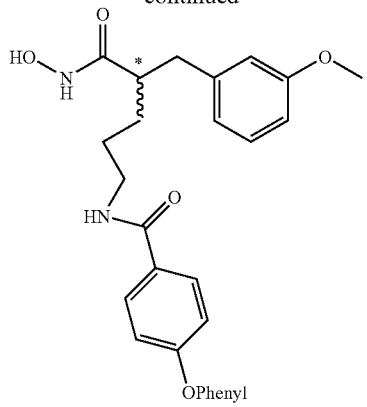

are not included in the invention as novel composition of matter.

The present invention also relates to pharmaceutical compositions suitable for administration to mammals, including humans, which include one or more compounds of the invention and are used for treatment or prevention of anthrax poisoning.

Biological Activity, Modes of Administration

Determining Biological Activity

As briefly noted above in the introductory section of this application for patent, the most serious, often lethal results of anthrax poisoning are caused by a toxin that is released by *bacillus anthracis* within the host. The toxin includes three proteins, one of which is a zinc-dependent metalloprotease enzyme (lethal factor) that cleaves near the N termini of several MAP kinase kinase enzymes (MKKS) of the host. It is this disruption of key signaling pathways mediated by the host MKK enzymes that result in the severe and often lethal results of infection by the bacteria.

An assay for identifying and measuring the effectiveness of potential drugs to treat anthrax poisoning is based on measuring the inhibitory effect of the candidate compound on the lethal factor enzyme. The procedure used in the present invention to measure the potential efficiency of the compounds of the present invention is based, in a somewhat modified form, on the assay described by Cummings et al., A peptide-based fluorescence resonance energy transfer assay for *Bacillus anthracis* lethal factor protease, PNAS, May 14, 2002, Vol 99, No. 10 6603-6606, expressly incorporated herein by reference. The gist of this assay that a fluorogenic peptide substrate is incubated with the lethal factor enzyme in the presence of the inhibitor and the inhibition of the lethal factor is measured by measuring the fluorescence intensity of the cleaved substrate. A description of the actual assay conditions used for evaluating the compounds of the present invention is provided below.

Assay Procedure

Inhibitors were solubilized in 100% DMSO at 10 mM, then diluted to the final desired concentration and 10% final DMSO in the assay. Lethal factor protease (20 nM) and inhibitor were briefly incubated at room temperature in the assay buffer (20 mM Hepes, 0.05% Tween 20, 0.02% $NaN_3$, pH 7.4), and the reaction started by the addition of 12.5 μM final of the fluorogenic peptide substrate, MAPKKide™ (List Biological Laboratories, Inc, Campbell, Calif.). The final volume was 50 μL, in half area black microtiter plates (Costar). Fluorescence intensity (Ex: 320 nm, Em: 420 nm) was monitored for 15 minutes at room temperature (Gemini XS, Molecular Devices), and the $K_i^{app}$ values were calculated using the program BatchKi (BioKin Ltd., Pullman, Wash.). Generally speaking a compound is considered active in this assay if the calculated $K_i^{app}$ value is less than 300 (<300) μM.

Modes of Administration

The compounds of the invention are useful for treating anthrax poisoning. The compounds of this invention may be administered systemically through oral, intravenous or other modes of systemic administration, depending on such considerations as the severity of the anthrax infection treated, quantity of drug to be administered, and numerous other considerations. For oral administration the drug may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate the compounds of the invention in suppository form or as extended release formulation for deposit under the skin or intramuscular injection. For each type of administration appropriate pharmaceutical excipients are likely to be added to the drug. The nature of such excipients for each type of systemic administration is well known in the art and need not be described here further.

A useful therapeutic or prophylactic concentration will vary from with the precise identity of the drug, with the severity of the anthrax infection being treated and the patient's susceptibility to treatment. Accordingly, no single concentration will be uniformly useful, but will require modification depending on the particularities of each situation. However, it is anticipated that an amount between 0.1 and 10 mg per kg of body weight per day will affect a therapeutic result.

Results of the Assay Measuring Lethal Factor Inhibitory Activity

Specific examples of compounds within the scope of the present invention are shown by their respective structural formulas in Tables 1 through 4 and their activity in the above-described assay is also indicated.

TABLE 1

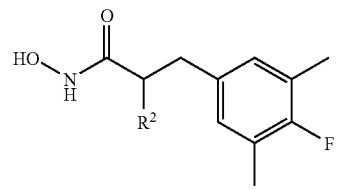

| Compound # | Ar | LF(FRET) $\overline{K_i^{app} \mu M)}$ |
|---|---|---|
| 167550 | Ph— | 65.2 |
| 167266 | 3-Me-4-F—Ph— | 2.3 |
| 167533 | 3,5-diMe-4-F—Ph— | 1.2 |

TABLE 2

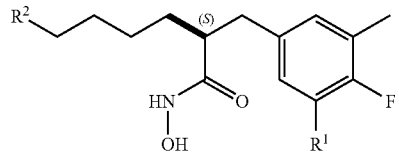

| Compound # | $R^2$ | LF(FRET) $\overline{K_i^{app} \mu M)}$ |
|---|---|---|
| 167857 | —H | 1.34 |
| 167858 | (R,S)-Me | 0.40 |
| 167914 | (R,S)-CN | 47.5 |
| 167856 | (R,S) 4-Br—Ph | 0.62 |
| 168009 | (R) 4-Br—Ph | 0.77 |
| 167973 | (S) 4-Br—Ph | 5.7 |
| 168051 | (R)-(E)-(CH$_2$)$_3$CH=CH-iPr | 51.6 |
| 168052 | (R)-(CH$_2$)$_5$-iPr | 300 |
| 168023 | (S)-(E)-(CH$_2$)$_3$CH=CH-iPr | 1.97 |
| 168031 | (S)-(CH$_2$)$_5$-iPr | 2.66 |

TABLE 3

| Compound # | $R^1$ | $R^2$ | LF(FRET) $\overline{K_i^{app} \mu M)}$ |
|---|---|---|---|
| 168171 | Me | —NH-(2-propyl-pentyl) | 0.25 |
| 168170 | Me | —NH—CH$_2$-cyclohexyl | 0.40 |
| 168149 | Me | —NH—CH$_2$—Ph | 0.13 |
| 168132 | Me | —NH-(4-F—Ph) | 2.24 |
| 168139 | H | —NH—CH$_2$-(3-Me-4-F—Ph) | 0.28 |
| 168050 | Me | —NH—CH$_2$-(3-Me-4-F—Ph) | 0.074 |
| 168117 | Me | —NH—CH$_2$-(4-F—Ph) | 0.045 |
| 168122 | Me | —NH—(CH$_2$)$_2$-(4-F—Ph) | 0.065 |
| 168123 | Me | —NH—(CH$_2$)$_3$-(4-F—Ph) | 0.047 |
| 168125 | Me | —NH—CH$_2$-(4-Cl—Ph) | 0.19 |
| 168140 | H | —NH—CH$_2$-(3-Ph—Ph) | 0.70 |
| 168141 | Me | —O—CH$_2$-(3-Me-4-F—Ph) | 3.60 |
| 168126 | Me | —N(Me)—CH$_2$-(4-F—Ph) | 0.55 |
| 168124 | Me | —(CH$_2$)$_2$-(4-F—Ph) | 10.3 |
| 168148 | Me | —NH—CH$_2$-5-(benzo[1,3]dioxolyl) | 0.22 |
| 168157 | Me | —NH—CH$_2$-2-(5-methylfuranyl) | 0.13 |
| 168179 | Me | —NH—CH$_2$-2-pyrazinyl | 0.71 |
| 168180 | Me | —NH—CH$_2$-2-benzo[b]thienyl | 0.40 |

TABLE 4

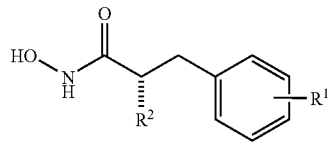

| PT | R[1] | R[2] | LF (FRET) $\overline{K_i^{app} \mu M)}$ |
|---|---|---|---|
| 168150 | 4-Cl | (S) —(CH$_2$)$_2$N(Me)—(CH$_2$)$_3$-(3-Me-4-F—Ph) | 1.75 |
| 168156 | 4-Cl | (S) —(CH$_2$)$_2$N(Me)—(CH$_2$)$_3$-(3,5-diMe-4-F—Ph) | 3.29 |
| 168134 | 4-Cl | (S) —(CH$_2$)$_6$-(3-Me-4-F—Ph) | 64.5 |
| 168164 | 3-Cl, 4-F | (S) —(CH$_2$)$_4$—N(Me)—CH$_2$-(4-F—Ph) | 0.20 |
| 168172 | 3,5-diMe, 4-F | (S) —(CH$_2$)$_2$N(Me)—(CH$_2$)$_3$-(4-F—Ph) | 0.29 |

GENERAL EMBODIMENTS AND SYNTHETIC METHODOLOGY

Definitions

The term alkyl refers to and covers any and all groups which are known as normal alkyl and branched-chain alkyl. Unless specified otherwise, lower alkyl means the above-defined broad definition of alkyl groups having 1 to 6 carbons in case of normal lower alkyl, and 3 to 6 carbons for lower branch chained alkyl groups. A pharmaceutically acceptable salt may be prepared for any compound used in accordance with the invention having a functionality capable of forming a salt, for example an acid or an amino functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids. Preferred salts are those formed with inorganic acids such as hydrochloric acid, sulfuric acid or phosphoric acid. Any of a number of simple organic acids such as mono-, di- or tri-acid may also be used.

Some compounds used in accordance with the present invention may have trans and cis (E and Z) isomers. Unless specific orientation of substituents relative to a double bond or a ring is indicated in the name of the respective compound, and/or by specifically showing in the structural formula the orientation of the substituents relative to the double bond or ring the invention covers trans as well as cis isomers.

Some of the compounds used in accordance with the present invention may contain one or more chiral centers and therefore may exist in enantiomeric and diastereomeric forms. The scope of the present invention is intended to cover all isomers per se, as well as mixtures of cis and trans isomers, mixtures of diastereomers, pure enantiomers (optical isomers) and 50:50 (racemic) or other ratio mixtures of enantiomers as well. In some cases one compound of a diastereomeric species, or one specific enantiomer of a chiral compound is more active than the other diastereomer(s) or optical isomer, and when such a case is established it is indicated in the respective designation of the compound.

General Synthetic Methodology

The novel compounds used in accordance with the invention are encompassed by the general Formula 1 provided above.

A general route for the synthesis of the compounds of Formula 1 is shown in the General Scheme 1, below.

Referring now to General Scheme 1 a derivative of malonic acid and a substituted benzaldehyde serve as starting materials. The variables R[1], m and R[2] are as defined in Formula 1. Such starting materials are either available commercially or can be obtained in accordance with known chemical scientific and or patent literature or by such modifications of known synthetic procedures which will be readily apparent to those skilled in the art. The malonic acid derivative and the substituted benzaldehyde are reacted in a suitable solvent, such as a mixture of piperidine and pyridine to give the compound shown in the scheme as Intermediate Formula 1. The olefinic double bond in the latter compound is saturated by hydrogenation to give the compound shown as Intermediate Formula 2. Intermediate Formula 2 is then reacted with O-(tetrahydropyran-2-yl)-hydroxylamine in the presence of 1-hydroxybenzotriazole (HOBt) and N-methylmorpholine (NMM) to give the compound of Intermediate Formula 3. The tetrahydropyranyl group is removed from Intermediate Formula 3 by treatment with trifluoroacetic acid (TFA) in a suitable aprotic solvent, such as dichloromethane (DCM) to give the compounds of Formula 1.

General Synthetic Scheme 1

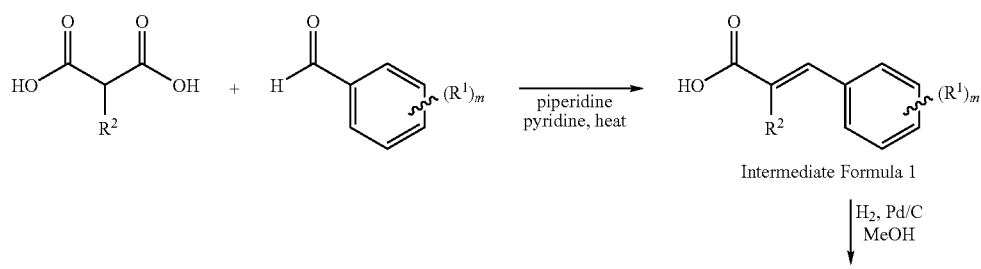

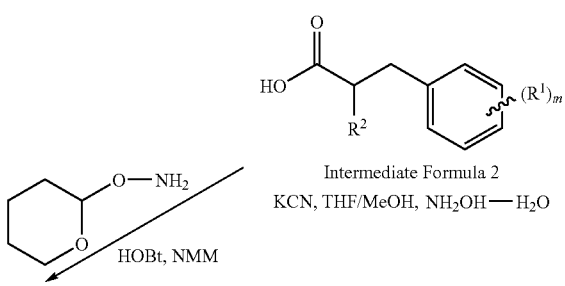

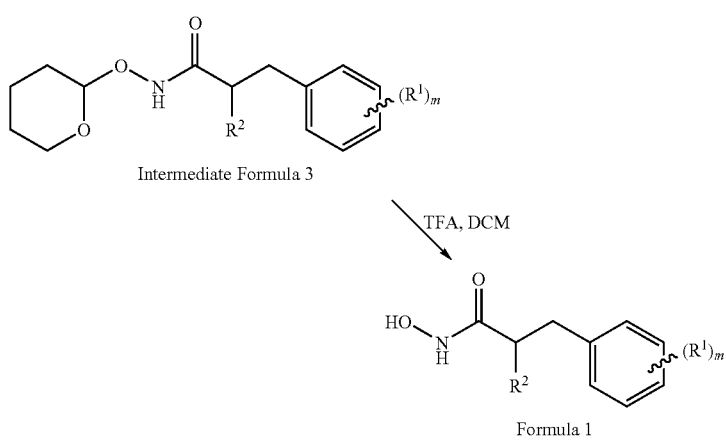

General Synthetic Scheme 2 discloses a synthetic route to a particular class of compounds of the invention which are shown in Tables 1 and 2. The starting materials in this scheme is a triphenylphosphine compounds (Wittig reagent) that can be obtained in accordance with well known synthetic procedures from compounds that are themselves readily available commercially or from the chemical literature. The triphenylphosphine compound is reacted with a benzaldehyde substituted with 0 to 3 $(R^1)_m$ groups to provide the Intermediate Formula 4 in a suitable solvent, such as THF and with heating. The variable symbols n, m and $R^1$ are defined as in connection with Formula 1. The Intermediate Formula 4 is then subjected to catalytic hydrogenation in methanol to give Intermediate Formula 5. The Intermediate Formula 5 is subjected to treatment with potassium cyanide (KCN) and hydroxylamine (NH₂OH—H₂O) in the presence of a suitable solvent or solvent mixture, such as tetrahydrofuran (THF) and methanol (MeOH) to provide compounds of Formula 2. The compounds of Formula 2 represent a subgenus of the compounds of Formula 1.

the Intermediate Formula 7. The olefinic bond of the Intermediate Formula 7 is oxidized and converted into an aldehyde function by treatment with ozone, followed by decomposition of the intermediate ozonide by treatment with dimethylsulfide (Me₂S) in dichloromethane to provide Intermediate Formula 8. The Intermediate Formula 8 is made into a Shiff base

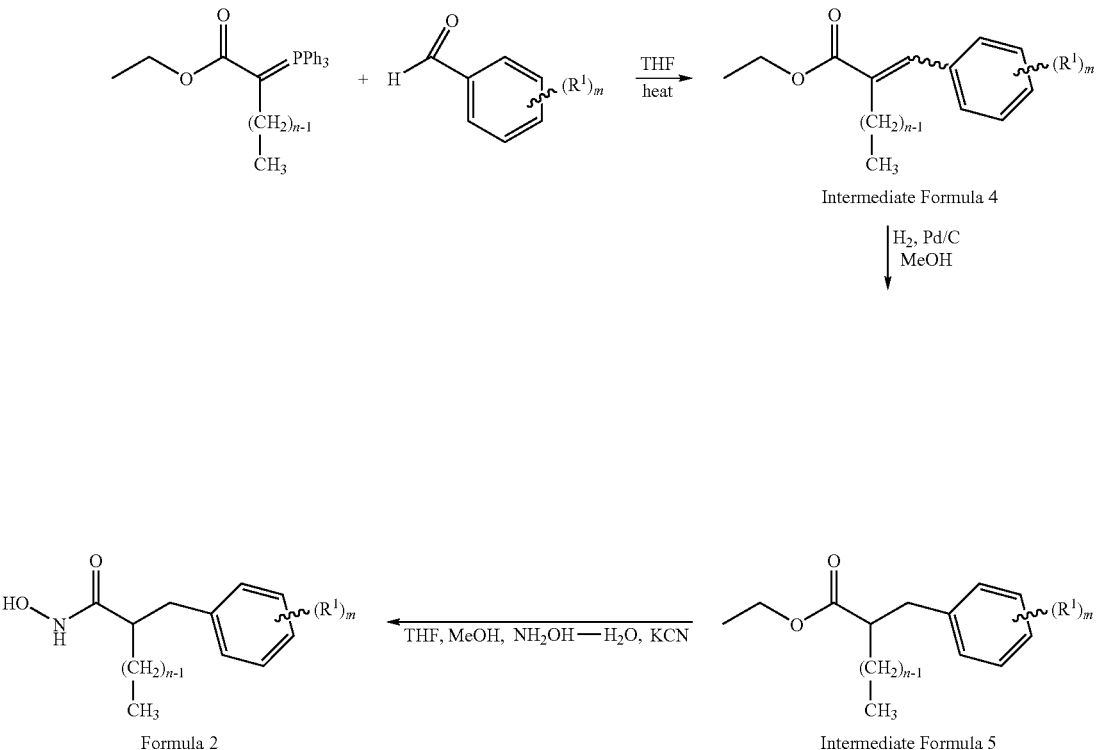

with phenylalkylamine shown in the scheme, and the Schiff base is reduced to provide the Intermediate Formula 9.

The Intermediate Formula 9 is converted to the hydroxamic acid compound of Formula 3 by treatment with potassium cyanide (KCN) and hydroxylamine (NH₂OH—H₂O) in the presence of a suitable solvent or solvent mixture, such as tetrahydrofuran (THF) and methanol (MeOH). The compounds of Formula 3 are within the scope of the invention and represent a subgenus of the compounds of Formula 1.

Specific Scheme 6 below discloses a method of preparing [3-(4-fluoro-phenyl)-propyl]-methyl-amine that serves as intermediate (C6) in the preparation of a compound that itself is made in accordance with the procedure disclosed in General Scheme 3. A person having ordinary skill in the art can readily modify the specific procedure of synthesizing intermediate C6 to make other intermediates of like structure to be used for the synthesis of compounds of the invention as disclosed in General Scheme 3.

General Scheme 3 discloses a synthetic route to another particular class of compounds of the invention which are shown in Table 2 and wherein the R² group with reference to Formula 1 is (CH₂)ₙNHR⁴ and where R⁴ is (CH₂)ₚphenyl with the phenyl substituted with 0 to 3 R¹ groups. The variable symbols in General Scheme 3 have the same meaning as in connection with Formula 1. Unless otherwise indicated this is generally true in the descriptions of all of the general schemes. The starting material in this scheme is an alkenoic acid chloride that is readily available commercially or from the chemical literature. The alkenoic acid chloride is reacted with (R)-4-benzyloxazolidin-2-one (commercially available) in the presence of butyl lithium and in a suitable solvent or solvent mixture, such as THF and hexane to give the Intermediate Formula 6. The Intermediate Formula 6 is then reacted with a substituted benzyl bromide in the presence of lithium bis(trimethylsilyl)amide (LiHMDS) in THF to yield General Synthetic Scheme 3
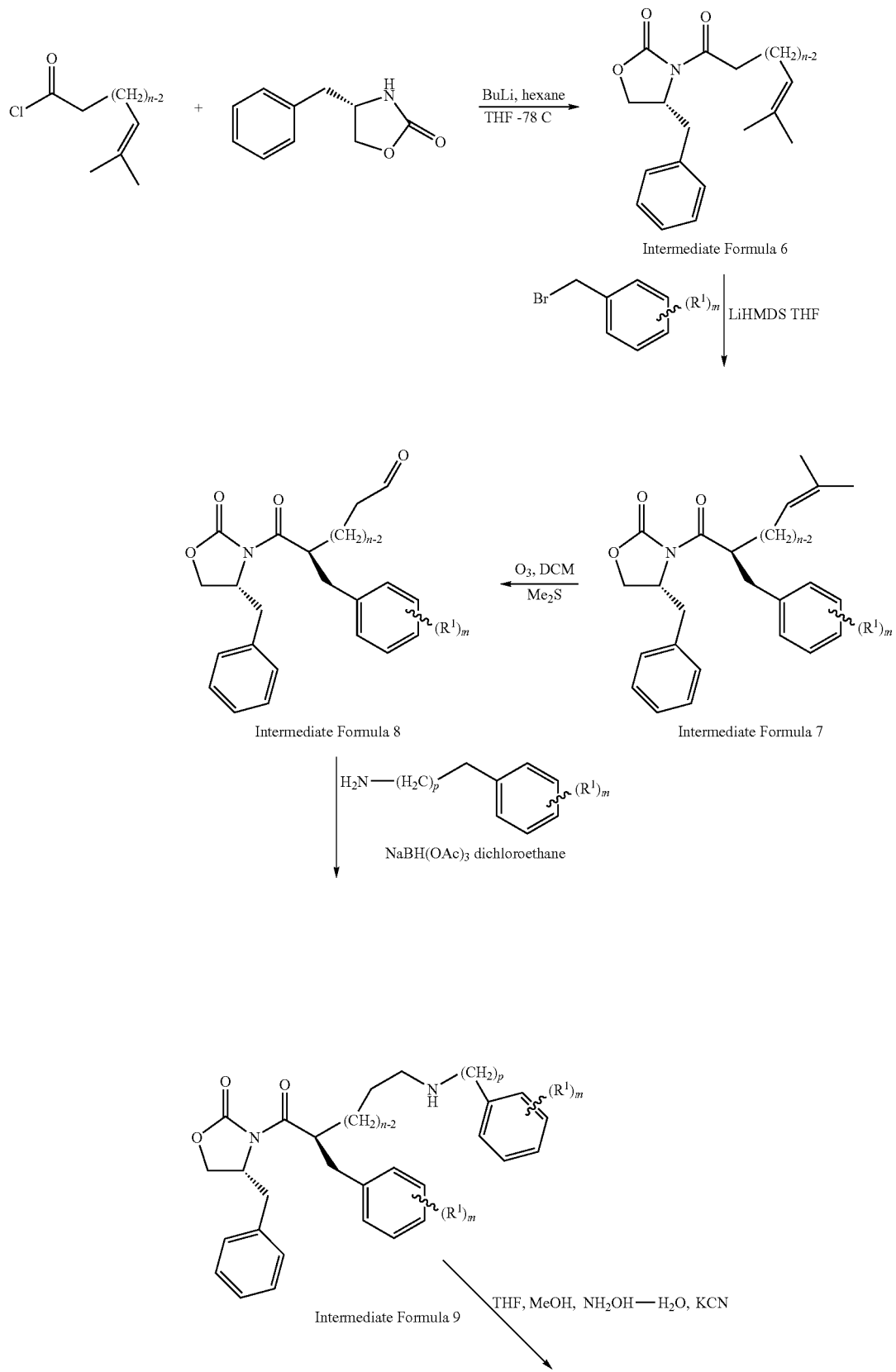

-continued

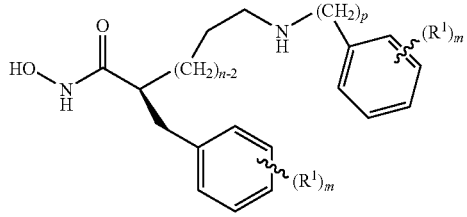

Formula 3

General Scheme 4 discloses a synthetic route to still another particular class of compounds of the invention which are shown in Table 2 and wherein the $R^2$ group with reference to Formula 1 is $(CH_2)_nOR^4$ and where $R^4$ is $(CH_2)_p$phenyl with the phenyl substituted with 0 to 3 $R^1$ groups. One starting material in this scheme is a lactone of an omega hydroxyl alkanoic acid. The variable n for this starting material has the same definition as in connection with Formula 1 with the restriction that the starting material must be able to form a cyclic lactone. The other starting material is a substituted phenylalkylbromide where the variables $R^1$, p and m have the same definition as in connection with Formula 1. These starting materials are reacted in the presence of strong base, such as KOH in a suitable solvent, such as toluene to provide the Intermediate of Formula 10. The Intermediate of Formula 10 is then reacted with (R)-4-benzyloxazolidin-2-one in the presence of triethylamine, pivaloyl chloride and LiCl in an aprotic solvent, such as THF, to give the Intermediate Formula 11. The Intermediate Formula 11 is then reacted with a substituted benzylbromide in the presence of LiHMDS in THF at cold temperature to give the Intermediate of Formula 12. The Intermediate Formula 12 is then converted to the hydroxamic acid compound of the invention of Formula 4 by treatment with potassium cyanide (KCN) and hydroxylamine ($NH_2OH$—$H_2O$) in the presence of a suitable solvent or solvent mixture, such as tetrahydrofuran (THF) and methanol (MeOH). The compounds of Formula 4 represent a subgenus of the compounds of Formula 1.

General Synthetic Scheme 4

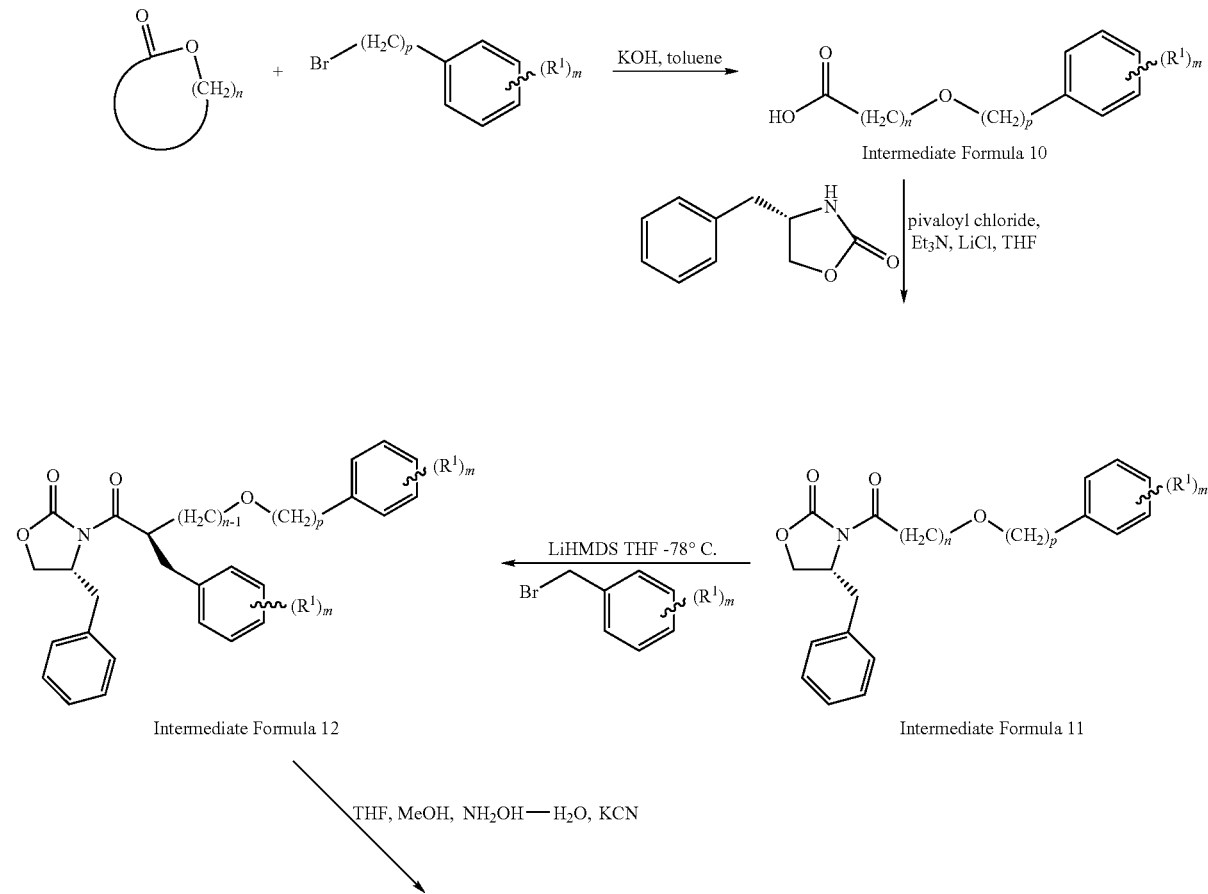

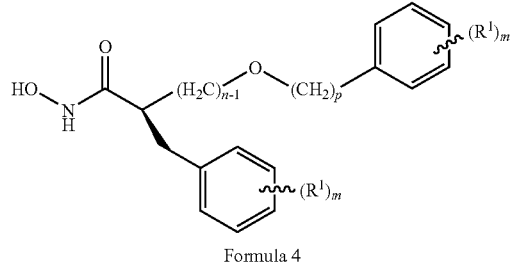

Formula 4

General Scheme 5 discloses a synthetic route to yet another particular class of compounds of the invention which are shown in Table 2 and wherein the $R^2$ group with reference to Formula 1 is alkylphenyl. In this reaction scheme the starting material is an omega bromo alkanoic acid where the variable n has the same definition as in connection with Formula 1. The omega bromo alkanoic acid is reacted with triphenylphosphine ($PPh_3$) in a suitable solvent, such as toluene, to provide the Intermediate Formula 13. The Intermediate Formula 13 is then reacted in a Wittig reaction with a substituted benzaldehyde to provide the Intermediate Formula 14. The variables $R^1$ and m in the formula of the substituted benzaldehyde are defined as in connection with Formula 1. The olefinic double bond of the Intermediate Formula 14 is reduced by catalytic hydrogenation to the carboxylic acid compound Intermediate Formula 15. The Intermediate Formula 15 is reacted with (R)-4-benzyloxazolidin-2-one in the presence of triethylamine, pivaloyl chloride and LiCl in an aprotic solvent, such as THF, to give the Intermediate Formula 16. Reaction of the Intermediate Formula 16 with a substituted bemzylbromide in the presence of LiHMDS in THF yields the Intermediate Formula 17. The Intermediate Formula 17 is then converted to the hydroxamic acid compound of the invention of Formula 5 by treatment with potassium cyanide (KCN) and hydroxylamine ($NH_2OH$—$H_2O$) in the presence of a suitable solvent or solvent mixture, such as tetrahydrofuran (THF) and methanol (MeOH). The compounds of Formula 5 are within the scope of the invention and represent a subgenus of the compounds of Formula 1.

General Synthetic Scheme 5

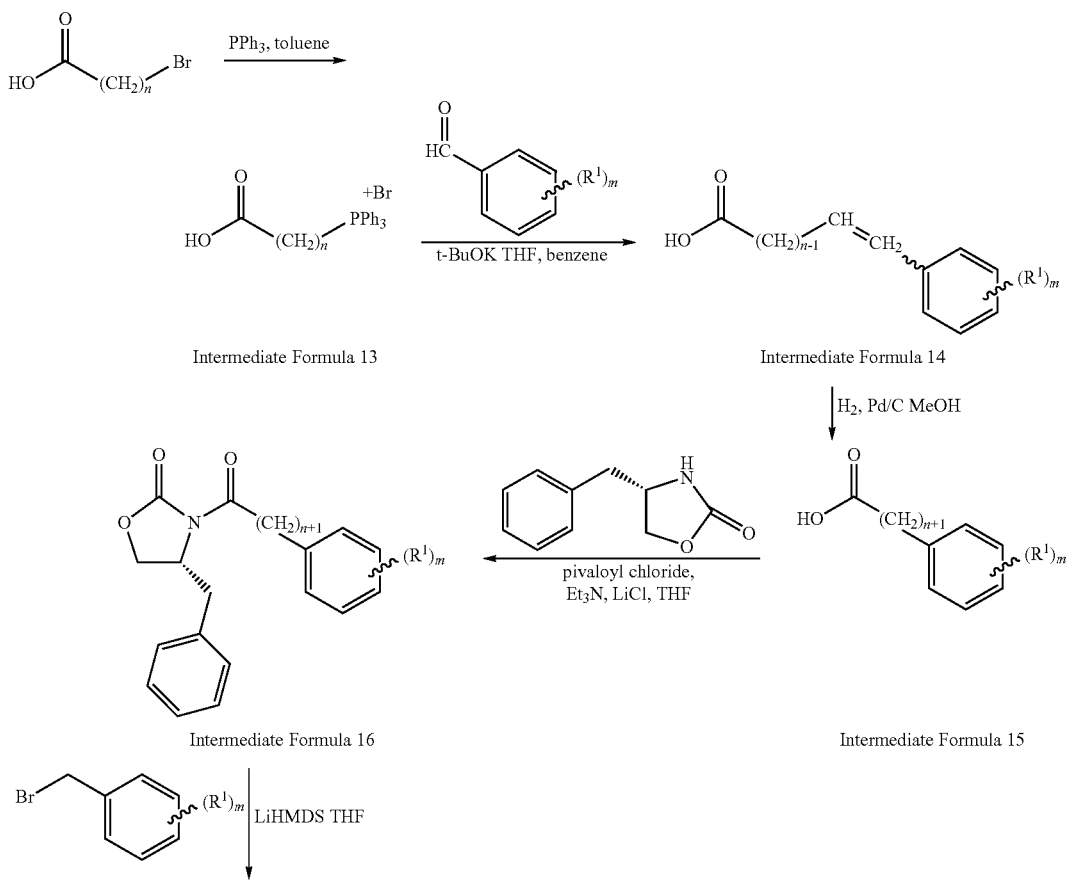

-continued

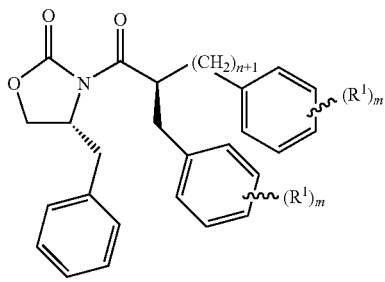

Intermediate Formula 17

THF, MeOH, NH$_2$OH—H$_2$O, KCN

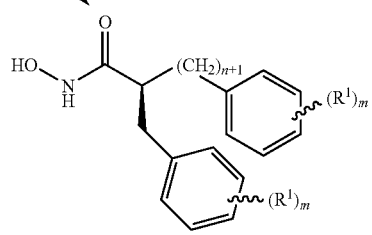

Formula 5

Preferred Examples

Referring now to the variable R$^1$ in Formula 1, in the compounds of the invention R$^1$ represents a substituent on the phenyl group shown in the formula. In the preferred compounds of the invention R$^1$ is F, Cl, methyl, methoxy or phenyl. The variable m is preferably the integer selected from 1, 2 and 3. Even more preferably the variable m is 2 or 3. Particularly preferred are compounds of the invention where m is 2, and the R$^1$ are methyl and fluoro, with the methyl group being in the 3 (meta) position and the fluoro being in the 4 (para) position. Also particularly preferred are compounds where m is 3, and there is a methyl group in the 3,5 (meta, meta) positions and a fluoro in the 4 (para) position of the phenyl ring.

Referring now to the variable R$^2$ in Formula 1 in the preferred compounds of the invention R$^2$ is CN, alkyl of 1 to 8 carbons, alkylphenyl where the alkyl group has 1 to 6 carbons, (CH$_2$)$_n$OCH$_2$-phenyl, (CH$_2$)$_n$CF$_3$ where n is 1 to 6, CH$_2$OR$^3$ where R$_3$ is H or t-butyl. In some preferred compounds R$^2$ is H. Compounds are also preferred where R$^2$ is an alkenyl group having 2 to 8 carbon atoms and one double bond, where R$^2$ is (CH$_2$)$_n$NHR$^4$ where the R group is alkylphenyl or alkylheteroaryl, alkylheteroaryl condensed with a benzene ring, where the phenyl or heteroaryl can be substituted with 0 to 3 R$^1$ groups, or R$^4$ is alkylcyclohexyl Compounds are also preferred where R$^2$ is (CH$_2$)$_n$NR$^6$R$^4$ and R$^6$ is alkyl.

EXPERIMENTAL

Scheme and experimental descriptions for the synthesis of the specific exemplary compounds are given below. The LC/MS data given was obtained using the following conditions: LC/MSD/ELSD analysis performed in ESI positive mode with an Agilent 1100 LC/MSD VL system equipped with Agilent 1100 HP PDA and Sedex 75 ELSD detectors. Column: Zorbax Eclipse SD-C18, 5 µm, 4.6×75 mm; Temperature set at 25° C.; Mobile Phase: % A=0.025% trifluoroacetic acid-water, % B=0.025% trifluoroacetic acid-acetonitrile; or: % A=0.10% formic acid-water, % B=0.10 formic acid-acetonitrile Linear Gradient: 20%-98% B in 15 min.; Flow rate: 1.0 mL/min.; ELSD gain set @ 3; UV set at 254 nm and 214 nm.

Specific Scheme 1

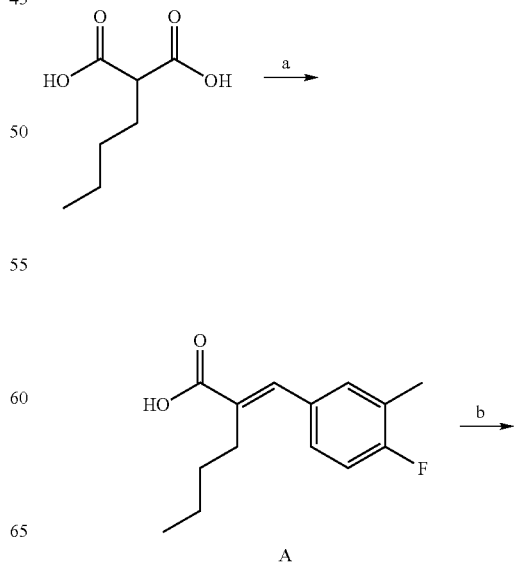

-continued

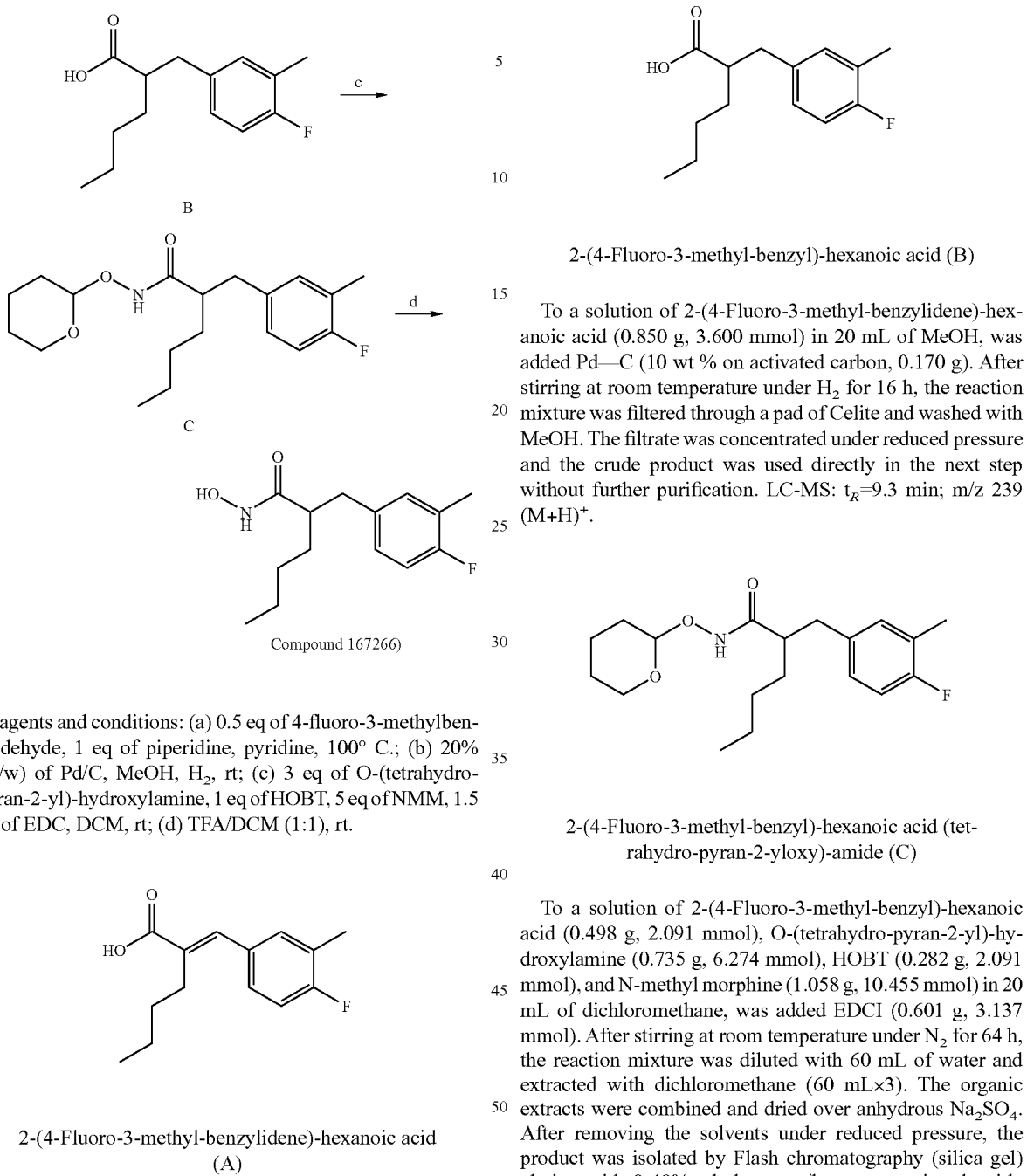

Compound 167266)

Reagents and conditions: (a) 0.5 eq of 4-fluoro-3-methylbenzaldehyde, 1 eq of piperidine, pyridine, 100° C.; (b) 20% (w/w) of Pd/C, MeOH, $H_2$, rt; (c) 3 eq of O-(tetrahydropyran-2-yl)-hydroxylamine, 1 eq of HOBT, 5 eq of NMM, 1.5 eq of EDC, DCM, rt; (d) TFA/DCM (1:1), rt.

2-(4-Fluoro-3-methyl-benzylidene)-hexanoic acid (A)

A mixture of 2-butyl-malonic acid (2.319 g, 14.482 mmol), 4-fluoro-3-methylbenzaldehyde (1.000 g, 7.241 mmol), and piperidine (1.232 g, 14.482 mmol) in 10 mL of pyridine was heated to 100° C. and stirred at this temperature for 16 h. After cooling to room temperature, the reaction mixture was poured into 25 mL of concentrated HCl containing 50 g of ice, and then extracted with ethyl acetate. The organic extracts were combined and dried over anhydrous $Na_2SO_4$, concentrated under reduced pressure, the product isolated by Flash chromatography (silica gel) eluting with 0-30% ethyl acetate/hexanes to give the title compound as yellow liquid (1.370 g, 80% yield). LC-MS: $t_R$=9.5 min; m/z 237 (M+H)$^+$.

2-(4-Fluoro-3-methyl-benzyl)-hexanoic acid (B)

To a solution of 2-(4-Fluoro-3-methyl-benzylidene)-hexanoic acid (0.850 g, 3.600 mmol) in 20 mL of MeOH, was added Pd—C (10 wt % on activated carbon, 0.170 g). After stirring at room temperature under $H_2$ for 16 h, the reaction mixture was filtered through a pad of Celite and washed with MeOH. The filtrate was concentrated under reduced pressure and the crude product was used directly in the next step without further purification. LC-MS: $t_R$=9.3 min; m/z 239 (M+H)$^+$.

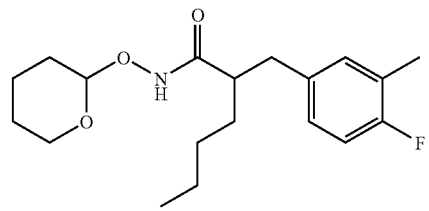

2-(4-Fluoro-3-methyl-benzyl)-hexanoic acid (tetrahydro-pyran-2-yloxy)-amide (C)

To a solution of 2-(4-Fluoro-3-methyl-benzyl)-hexanoic acid (0.498 g, 2.091 mmol), O-(tetrahydro-pyran-2-yl)-hydroxylamine (0.735 g, 6.274 mmol), HOBT (0.282 g, 2.091 mmol), and N-methyl morphine (1.058 g, 10.455 mmol) in 20 mL of dichloromethane, was added EDCI (0.601 g, 3.137 mmol). After stirring at room temperature under $N_2$ for 64 h, the reaction mixture was diluted with 60 mL of water and extracted with dichloromethane (60 mL×3). The organic extracts were combined and dried over anhydrous $Na_2SO_4$. After removing the solvents under reduced pressure, the product was isolated by Flash chromatography (silica gel) eluting with 0-40% ethyl acetate/hexanes to give the title compound as a pale yellow solid (0.423 g, 60% yield). LC-MS: $t_R$=9.1 min; m/z 338 (M+H)$^+$.

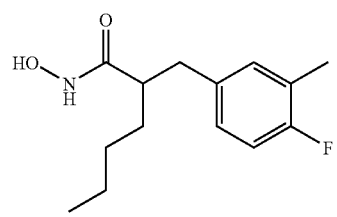

2-(4-Fluoro-3-methyl-benzyl)-hexanoic acid hydroxyamide (Compound 167266)

To a solution of 2-(4-Fluoro-3-methyl-benzyl)-hexanoic acid (tetrahydro-pyran-2-yloxy)-amide (0.0.358 g, 1.062 mmol) in 5 mL of dichloromethane, was added trifluoroacetic acid (5 mL). After stirring at room temperature for 3 h, the reaction mixture was concentrated under reduced pressure. The product was isolated by Flash chromatography (silica gel) eluting with 0-10% methanol/dichloromethane to give the title compound as an off-white solid (0.059 g, 22% yield). LC-MS: $t_R$=7.1 min; m/z 254 (M+H)$^+$; $^1$H NMR (300 MHz, CD$_3$OD) δ 0.89 (t, J=6.60 Hz, 3H), 1.27-1.36 (m, 4H), 1.39-1.49 (m, 1H), 1.60-1.67 (m, 1H), 2.23 (d, J=1.50 Hz, 3H), 2.24-2.32 (m, 1H), 2.62 (dd, J=13.50, 5.40 Hz, 1H), 2.79 (dd, J=13.50, 9.60 Hz, 1H), 6.88 (t, J=9.60 Hz, 1H), 6.95-6.96 (m, 1H), 7.01 (t, J=7.50 Hz, 1H).

Specific Scheme 2

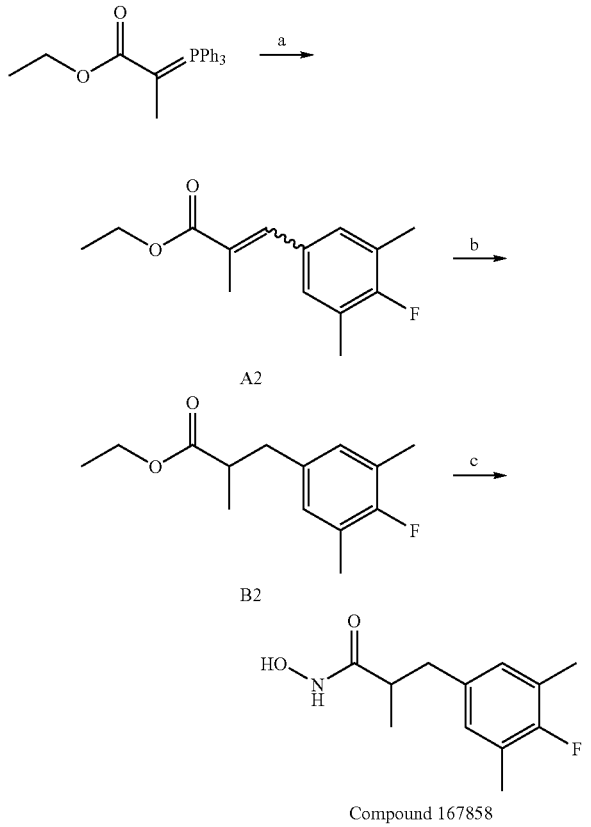

Compound 167858

Reagents and conditions: (a) 1 eq of 3,5-dimethyl-4-fluorobenzaldehyde, THF, microwave heating to 100° C.; (b) 20% (w/w) of Pd/C, MeOH, H$_2$, rt; (c) KCN (5 mol %), THF/MeOH/50% NH$_2$OH—H$_2$O (2:2:1), rt.

Ethyl 3-(4-fluoro-3,5-dimethylphenyl)-2-methylacrylate (A2)

Ethoxy-carbonylethylene triphenyl phosphorane (0.476 g, 1.314 mmol) and 3,5-dimethyl-4-fluorobenzaldehyde (0.200 g, 1.314 mmol) were weighed into a microwave tube followed by the addition of 3 mL of THF. After stirred under microwave irradiation at 100° C. for 1 h, the reaction mixture was concentrated under reduced pressure. The product was isolated by Flash column chromatography (silica gel column) eluting with 0-30% ethyl acetate/hexanes to give the title compound as a white solid (0.267 g, 86% yield). LC-MS: $t_R$=10.6 & 11.3 min; m/z 237 (M+H)$^+$.

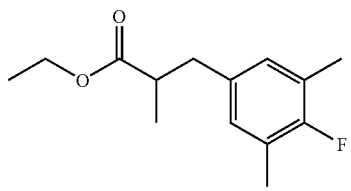

ethyl 2-(4-fluoro-3,5-dimethylbenzyl)propanoate (B2)

To a solution of Ethyl 3-(4-fluoro-3,5-dimethylphenyl)-2-methylacrylate (0.190 g, 0.855 mmol) in 10 mL of MeOH, was added Pd (10 wt % on activated carbon, 0.038 g). After stirring at room temperature under H$_2$ (1 atm) for 40 h, the reaction mixture was filtered through a pad of Celite and washed with MeOH. The filtrate was concentrated under reduced pressure. The crude product was used directly in the next step without further purification (0.138 g, 88% yield). LC-MS: $t_R$=10.9 min; m/z 239 (M+H)$^+$.

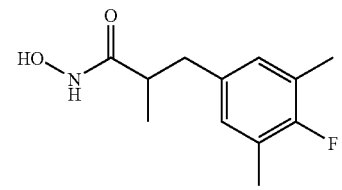

2-(4-fluoro-3,5-dimethylbenzyl)-N-hydroxypropanamide (Compound 167858)

To a solution of ethyl 2-(4-fluoro-3,5-dimethylbenzyl)propanoate (0.135 g, 0.567 mmol) in 5 mL of THF/MeOH/50% NH$_2$OH—H$_2$O (2:2:1), was added KCN (0.002 g, 0.028 mmol). After stirring at room temperature for 63 h, the reaction mixture was concentrated under reduced pressure. The product was isolated by Flash column chromatography (silica gel column) eluting with 0-10% methanol/dichloromethane to give the title compound as an off-white solid (0.045 g, 35% yield). LC-MS: $t_R$=5.8 min; m/z 226 (M+H)$^+$. $^1$H NMR (500 MHz, CD$_3$OD) δ 1.11 (d, J=6.88 Hz, 3H), 2.18 (d, J=1.68 Hz, 6H), 2.37-2.41 (m, 1H), 2.53 (dd, J=13.43, 6.38 Hz, 1H), 2.78 (dd, J=13.42, 8.89 Hz, 1H), 6.82 (d, J=7.05 Hz, 2H); $^{13}$C NMR (125.75 MHz, CD$_3$OD) δ 14.53 (d, J=4.15 Hz), 18.05, 40.04, 41.31, 125.02 (d, J=17.86 Hz), 130.44 (d, J=4.53 Hz), 135.91 (d, J=3.65 Hz), 160.83, 175.31

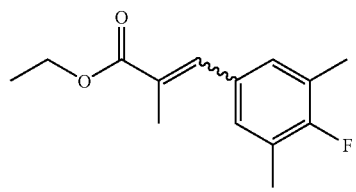

Specific Scheme 3

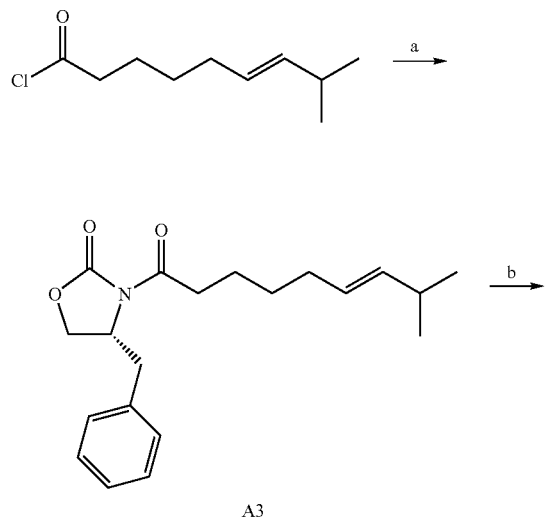

A3

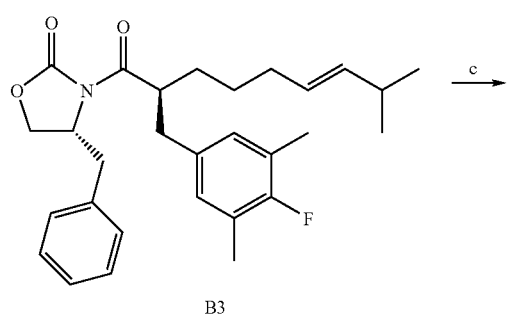

B3

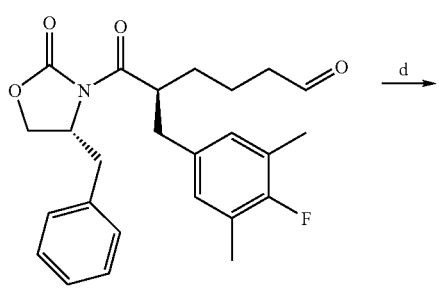

C3

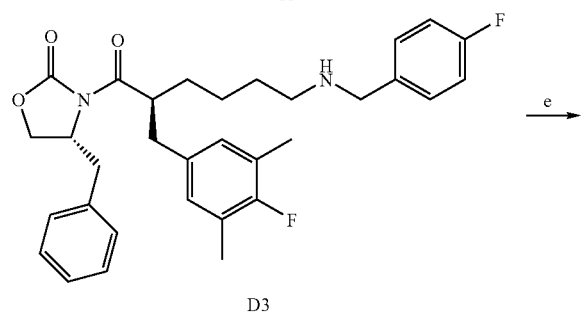

D3

-continued

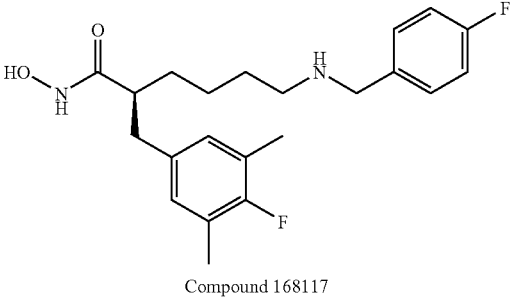

Compound 168117

Reagents and conditions: (a) 1 eq of (R)-4-benzyloxazolidin-2-one, 1 eq of n-BuLi (2.5 M in hexane), THF, −78° C. to rt; (b) 1.5 eq of LiHMDS (1.0 M in THF), 1.1 eq of 3,5-dimethyl-4-fluorobenzyl bromide, THF, −78° C. to rt; (c) O₃, 5 eq of Me₂S, DCM, −78° C. to rt; (d) 1.2 eq of 4-fluorobenzylamine, 1.4 eq of NaBH(OAc)₃, dichloroethane, rt; (e) KCN (5 mol %), THF/MeOH/50% NH₂OH—H₂O (2:2:1), rt.

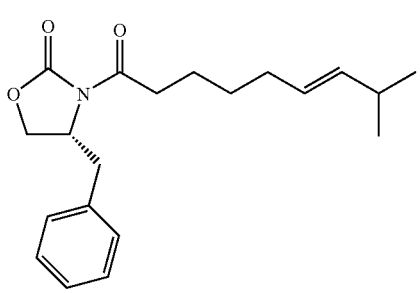

(R)-3-((E)-8-methylnon-6-enoyl)-4-benzyloxazolidin-2-one (A3)

To a cooled (−78° C.) solution of (R)-4-benzyloxazolidin-2-one (2.817 g, 15.899 mmol) in 40 mL of THF, was added n-BuLi (6.4 mL, 15.899 mmol, 2.5 M in hexane). The resulting mixture was stirred at −78° C. under N₂ for 15 min. and then (E)-8-methylnon-6-enoyl chloride (3.000 g, 15.899 mmol) was added. After stirring at −78° C. for 1 h and then being warmed to room temperature under N₂ for overnight, the reaction mixture was quenched with 80 mL of NH₄Cl solution and extracted with dichloromethane (60 mL×3). The combined organic extracts were dried (Na₂SO₄), filtered, and concentrated under reduced pressure. The product was isolated by Flash column chromatography (silica gel column) eluting with 0-30% ethyl acetate/hexanes to give the title compound as colorless oil (4.468 g, 85% yield). GC-MS: $t_R$=6.2 min; m/z 329 (M⁺).

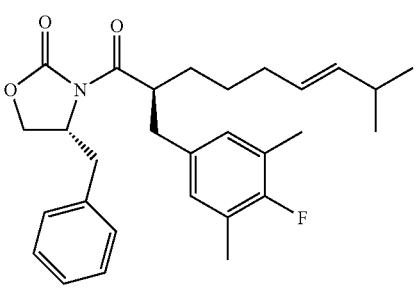

(R)-3-((S,E)-2-(4-fluoro-3,5-dimethylbenzyl)-8-methylnon-6-enoyl)-4-benzyloxazolidin-2-one (B3)

To a cooled (−78° C.) solution of (R)-3-((E)-8-methylnon-6-enoyl)-4-benzyloxazolidin-2-one (2.000 g, 6.071 mmol) in 40 mL of THF, was added LiHMDS (9.1 mL, 9.1 mmol, 1.0 M in THF). The resulting mixture was stirred at −78° C. under $N_2$ for 1 h and then a solution of 3,5-dimethyl-4-fluorobenzyl bromide (1.450 g, 6.678 mmol) in 10 mL of THF was added. After being stirred at −78° C. for 1 h the reaction mixture was warmed to room temperature for 2 h, and then quenched with 80 mL of $NH_4Cl$ solution and extracted with dichloromethane (60 mL×3). The combined organic extracts were dried ($Na_2SO_4$), filtered, and concentrated under reduced pressure. The product was isolated by Flash column chromatography (silica gel column) eluting with 0-100% dichloromethane/hexanes to give the title compound as colorless oil (1.925 g, 68% yield). GC-MS: $t_R$=8.8 min; m/z 465 ($M^+$).

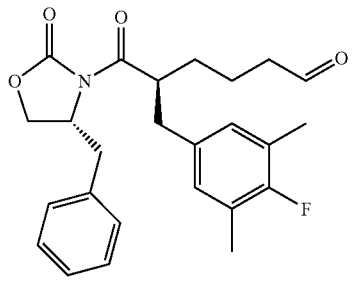

(S)-5-(4-fluoro-3,5-dimethylbenzyl)-6-((R)-4-benzyl-2-oxooxazolidin-3-yl)-6-oxohexanal (C3)

A solution of (R)-3-((S,E)-2-(4-fluoro-3,5-dimethylbenzyl)-8-methylnon-6-enoyl)-4-benzyloxazolidin-2-one (0.541 g, 1.162 mmol) in 10 mL of dichloromethane was cooled to −78° C. A stream of $O_3$ was bubbled through the solution until it became blue. The solution was sparged with $O_2$ was until the blue color disappeared. $Me_2S$ (0.43 mL, 5.810 mmol) was added and the solution warmed to room temperature and stirred for overnight. The reaction mixture was concentrated under reduced pressure and the product isolated by Flash column chromatography (silica gel column) eluting with 0-100% dichloromethane/hexanes to give the title compound as colorless oil (0.412 g, 83% yield). GC-MS: $t_R$=8.5 min; m/z 425 ($M^+$).

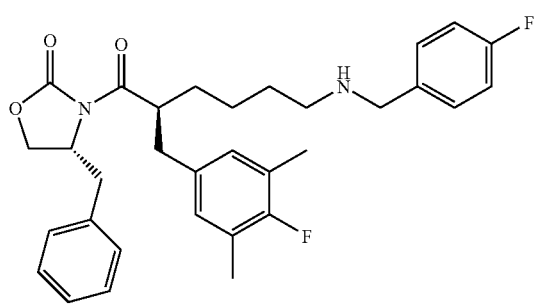

(R)-3-((S)-2-[4-fluoro-3,5-dimethylbenzyl)-6-(4-fluorobenzylamino)-hexanoyl]-4-benzyloxazolidin-2-one (D3)

To a solution of (S)-5-(4-fluoro-3,5-dimethylbenzyl)-6-((R)-4-benzyl-2-oxooxazolidin-3-yl)-6-oxohexanal (0.039 g, 0.0917 mmol) and 4-fluorobenzyl amine (0.014 g, 0.110 mmol) in 3 mL of dichloroethane, was added $NaBH(OAc)_3$ (0.027 g, 0.128 mmol). After stirring at room temperature for overnight, the reaction was quenched with 20 mL of saturated $NaHCO_3$ solution and the reaction mixture was extracted with ethyl acetate (20 mL×3). The combined organic extracts were dried ($Na_2SO_4$), filtered, and concentrated under reduced pressure. The product was isolated by Flash column chromatography (silica gel column) eluting with 0-10% methanol/dichloromethane to give the title compound as light yellow oil (0.030 g, 62% yield). LC-MS: $t_R$=6.9 min; m/z 535 $(M+H)^+$.

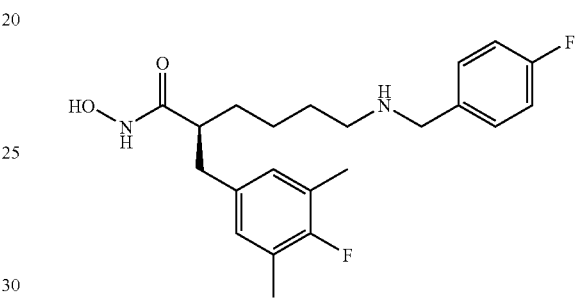

(S)-2-(4-fluoro-3,5-dimethylbenzyl)-6-(4-fluorobenzylamino)-N-hydroxyhexanamide (Compound 168117)

To a solution of (R)-3-((S)-2-[4-fluoro-3,5-dimethylbenzyl)-6-(4-fluorobenzylamino)-hexanoyl]-4-benzyloxazolidin-2-one (0.030 g, 0.0561 mmol) in 2.5 mL of THF/MeOH/50% $NH_2OH$—$H_2O$ (2:2:1), was added KCN (0.001 g, 0.015 mmol). After stirring at room temperature for overnight, the reaction mixture was acidified with concentrated HCl to pH=2 and filtered. The product was isolated by RP-HPLC eluting with 20-100% acetonitrile (0.025% TFA)/water (0.025% TFA) to give the title compound as an off-white solid (0.005 g, 23% yield). LC-MS: $t_R$=4.8 min, m/z 391 $(M+H)^+$, $^1$H NMR (300 MHz, $CD_3OD$) δ 1.27-1.38 (m, 2H), 1.40-1.57 (m, 2H), 1.58-1.75 (m, 2H), 2.19 (s, 6H), 2.20-2.31 (m, 1H), 2.52-2.66 (m, 1H), 2.70-2.82 (m, 1H), 3.00 (t, J=7.91 Hz, 2H), 4.17 (s, 2H), 6.82 (d, J=6.74 Hz, 2H), 7.20 (t, J=8.64 Hz, 2H), 7.51 (dd, J=8.20, 5.27 Hz, 2H).

Specific Scheme 4

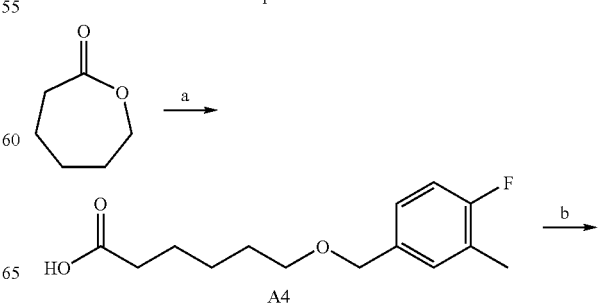

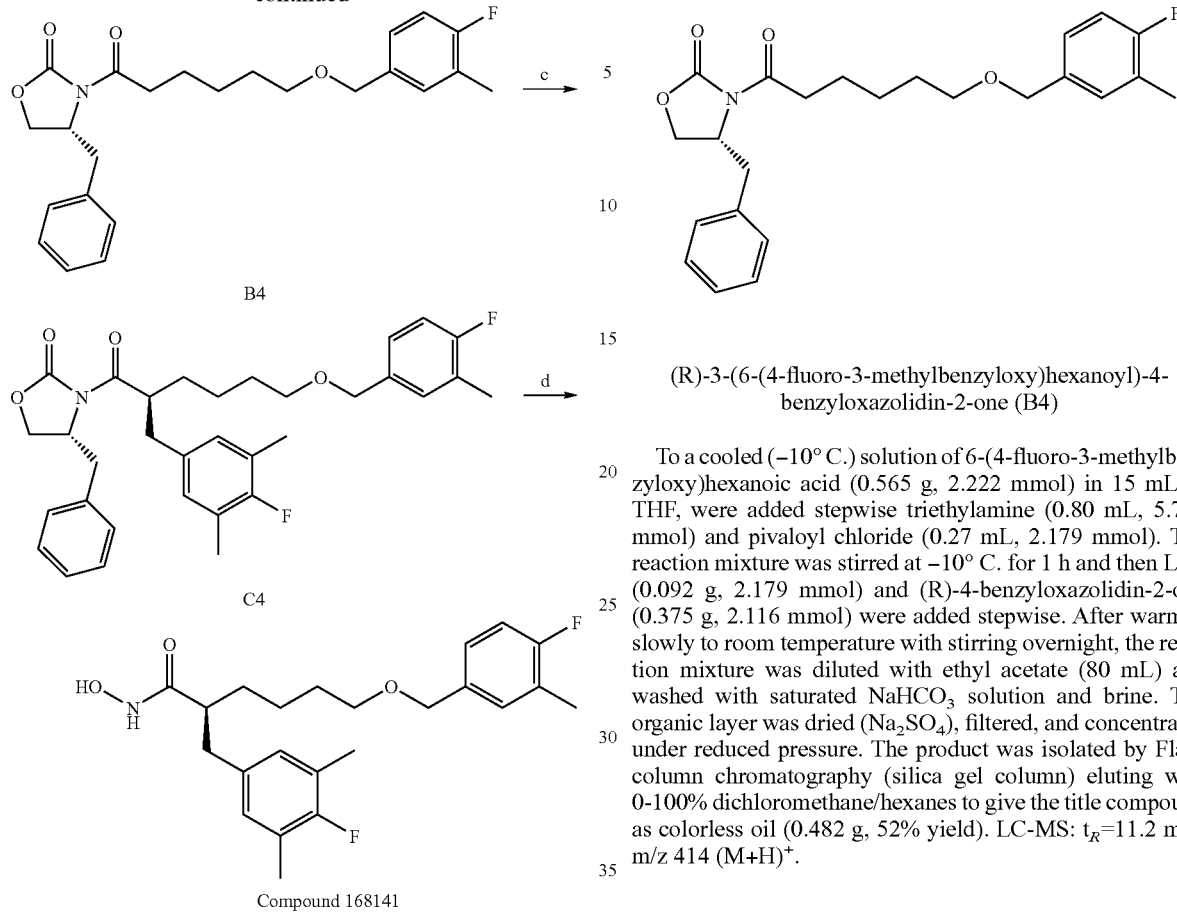

B4

C4

Compound 168141

Reagents and conditions: (a) 3 eq of 4-fluoro-3-methylbenzyl bromide, 5 eq of KOH, toluene, reflux; (b) 0.98 eq of pivaloyl chloride, 2.6 eq of Et$_3$N, 0.98 eq of LiCl, 0.95 eq of (R)-4-benzyloxazolidin-2-one, THF, −10° C. to rt; (c) 1.5 eq of LiHMDS (1.0 M in THF), 3 eq of 3,5-dimethyl-4-fluorobenzyl bromide, THF, −78° C. to rt; (d) KCN (5 mol %), THF/MeOH/50% NH$_2$OH—H$_2$O (2:2:1), rt.

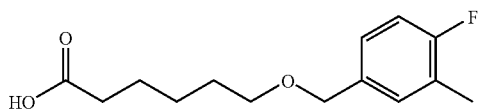

6-(4-fluoro-3-methylbenzyloxy)hexanoic acid (A4)

To a solution of oxepan-2-one (0.562 g, 4.925 mmol) and 4-fluoro-3-methylbenzyl bromide (3.000 g, 14.774 mmol) in 20 mL of toluene, was added KOH (1.382 g, 24.625 mmol). The mixture was refluxed for 86 h and after cooling to room temperature, the reaction mixture was diluted with water (80 mL) and washed with ether. The aqueous layer was acidified with concentrated HCl to pH=2 and extracted with ether (50 mL×3). The combined organic extracts were dried (Na$_2$SO$_4$), filtered, and concentrated under reduced pressure to give the title compound as colorless oil which was used directly in the next step without further purification (1.173 g, 94% yield). LC-MS: t$_R$=8.0 min, m/z 277 (M+H)$^+$.

(R)-3-(6-(4-fluoro-3-methylbenzyloxy)hexanoyl)-4-benzyloxazolidin-2-one (B4)

To a cooled (−10° C.) solution of 6-(4-fluoro-3-methylbenzyloxy)hexanoic acid (0.565 g, 2.222 mmol) in 15 mL of THF, were added stepwise triethylamine (0.80 mL, 5.713 mmol) and pivaloyl chloride (0.27 mL, 2.179 mmol). The reaction mixture was stirred at −10° C. for 1 h and then LiCl (0.092 g, 2.179 mmol) and (R)-4-benzyloxazolidin-2-one (0.375 g, 2.116 mmol) were added stepwise. After warmed slowly to room temperature with stirring overnight, the reaction mixture was diluted with ethyl acetate (80 mL) and washed with saturated NaHCO$_3$ solution and brine. The organic layer was dried (Na$_2$SO$_4$), filtered, and concentrated under reduced pressure. The product was isolated by Flash column chromatography (silica gel column) eluting with 0-100% dichloromethane/hexanes to give the title compound as colorless oil (0.482 g, 52% yield). LC-MS: t$_R$=11.2 min; m/z 414 (M+H)$^+$.

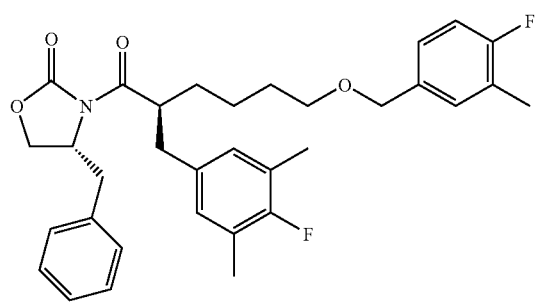

(R)-3-((S)-2-(4-fluoro-3,5-dimethylbenzyl)-6-(4-fluoro-3-methylbenzyloxy)hexanoyl)-4-benzyloxazolidin-2-one (C4)

To a cooled (−78° C.) solution of (R)-3-(6-(4-fluoro-3-methylbenzyloxy)hexanoyl)-4-benzyloxazolidin-2-one (0.220 g, 0.532 mmol) in 5 mL of THF, was added LiHMDS (0.80 mL, 0.80 mmol, 1.0 M in THF). The resulting mixture was stirred at −78° C. under N$_2$ for 1 h and then a solution of 3,5-dimethyl-4-fluorobenzyl bromide (0.346 g, 1.596 mmol) in 3 mL of THF was added. After stirring at −78° C. for 1 h the reaction mixture was warmed to room temperature for 2 h, and then quenched with 20 mL of NH$_4$Cl solution and extracted with dichloromethane (20 mL×3). The combined organic extracts were dried (Na$_2$SO$_4$), filtered, and concentrated under reduced pressure. The product was isolated by Flash column chromatography (silica gel column) eluting with 0-100% dichloromethane/hexanes to give the title compound as colorless oil (0.106 g, 36% yield). GC-MS: $t_R$=15.6 min; m/z 549 (M+).

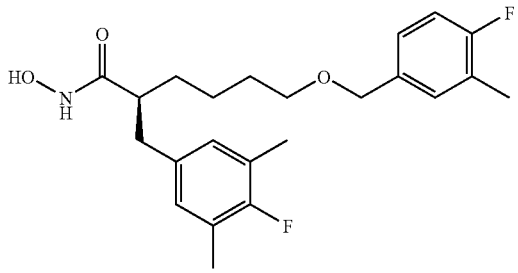

(S)-2-(4-fluoro-3,5-dimethylbenzyl)-6-(4-fluoro-3-methylbenzyloxy)-N-hydroxyhexanamide (Compound 168141)

To a solution of (R)-3-((S)-2-(4-fluoro-3,5-dimethylbenzyl)-6-(4-fluoro-3-methylbenzyloxy)hexanoyl)-4-benzyloxazolidin-2-one (0.040 g, 0.0728 mmol) in 2.5 mL of THF/MeOH/50% NH$_2$OH—H$_2$O (2:2:1), KCN (0.001 g, 0.015 mmol) was added. After stirring at room temperature for overnight, the reaction mixture was acidified with concentrated HCl to pH=2 and filtered. The filtrate was purified by RP-HPLC eluting with 20-100% acetonitrile (0.025% TFA)/water (0.025% TFA) to give the title compound as an off-white solid (0.005 g, 23% yield). LC-MS: $t_R$=9.6 min, m/z 406 (M+H)+; 1H NMR (300 MHz, CD$_3$OD) δ 1.28-1.51 (m, 4H), 1.52-1.70 (m, 2H), 2.18 (s, 6H), 2.25 (s, 3H), 2.26-2.33 (m, 1H), 2.52-2.63 (m, 1H), 2.68-2.79 (m, 1H), 3.44 (t, J=6.30 Hz, 2H), 4.40 (s, 2H), 6.81 (d, J=7.03 Hz, 2H), 6.97 (t, J=9.08 Hz, 1H), 7.09-7.15 (m, 1H), 7.18 (d, J=7.32 Hz, 1H).

Specific Scheme 5

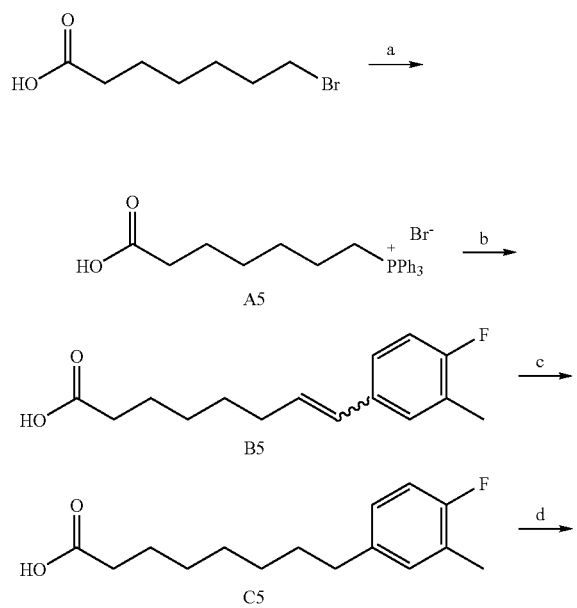

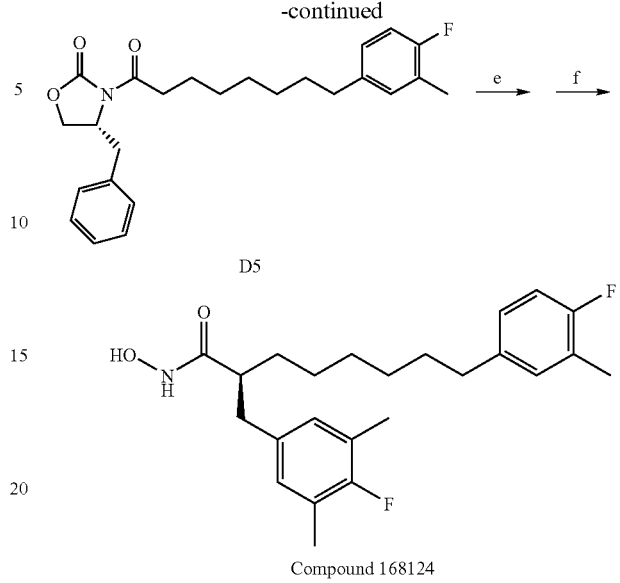

Reagents and conditions: (a) 1.1 eq of PPh$_3$, toluene, reflux; (b) 0.6 eq of 4-fluoro-3-methylbenzaldehyde, 3 eq of t-BuOK (1M in THF), benzene, reflux; (c) H$_2$, 20% (w/w) of Pd/C, MeOH; (d) 1.1 eq of pivaloyl chloride, 2.7 eq of Et$_3$N, 1.1 eq of LiCl, 1.1 eq of (R)-4-benzyloxazolidin-2-one, THF, −10° C. to rt; (e) 1.5 eq of LiHMDS (1.0 M in THF), 3 eq of 3,5-dimethyl-4-fluorobenzyl bromide, THF, −78° C. to rt; (f) KCN (5 mol %), THF/MeOH/50% NH$_2$OH—H$_2$O (2:2:1), rt.

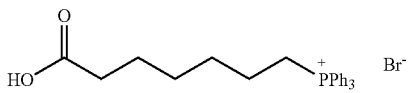

7-Carboxyheptanyltriphenylphosphonium bromide (A5)

A solution of 7-bromoheptanoic acid (5.000 g, 23.913 mmol) and PPh$_3$ (6.899 g, 26.304 mmol) in 50 mL of toluene was refluxed for 63 h. After cooling to room temperature, the solvent was removed under reduced pressure and the residue was tritited with ether three times and dried in vacuum to give the title compound as a white foam solid (9.240 g, 82% yield).

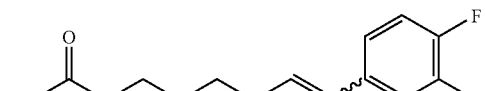

8-(4-fluoro-3-methylphenyl)oct-7-enoic acid (B5)

To a suspension of 7-Carboxyheptanyltriphenylphosphonium bromide (9.240 g, 19.602 mmol) in 100 mL of benzene, was added t-BuOK (58.8 mL, 58.8 mmol, 1M in THF). The resulting mixture was refluxed for 1 h and then 4-fluoro-3-methylbenzaldehyde (1.43 mL, 11.761 mmol) was added via a syringe. The mixture was continued to reflux under N₂ for 63 h. After cooling to room temperature, the reaction mixture was washed with water (80 mL). The aqueous layer was acidified with concentrated HCl to pH=2 and extracted with ethyl acetate (30 mL×3). The combined organic extracts were dried (Na₂SO₄), filtered, and concentrated under reduced pressure. The product was isolated by Flash column chromatography (silica gel column) eluting with 0-30% ethyl acetate/hexanes to give the title compound as colorless oil (3.150 g, >99% yield). LC-MS: $t_R$=9.6 min, m/z 251 (M+H)⁺.

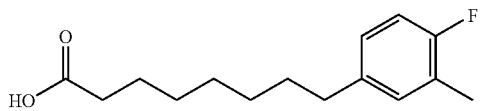

8-(4-fluoro-3-methylphenyl)octanoic acid (C5)

To a solution of 8-(4-fluoro-3-methylphenyl)oct-7-enoic acid (0.976 g, 3.899 mmol) in 30 mL of MeOH, was added 10% Pd on C (0.195 g). After stirring at room temperature under H₂ for 63 h, the reaction mixture was filtered through a pad of Celite and washed with ethyl acetate. The filtrate was concentrated under reduced pressure. The residue was used directly in the next step without further purification (0.938 g, 95% yield). LC-MS: $t_R$=10.1 min, m/z 253 (M+H)⁺.

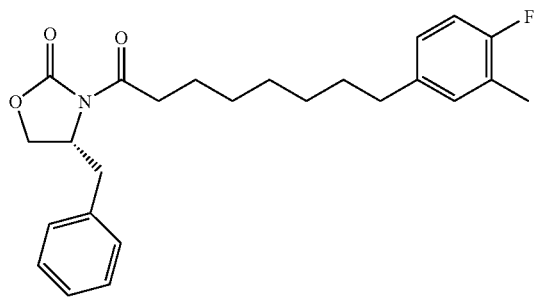

(R)-3-(8-(4-fluoro-3-methylphenyl)octanoyl)-4-benzyloxazolidin-2-one (D5)

To a cooled (−10° C.) solution of 8-(4-fluoro-3-methylphenyl)octanoic acid (0.452 g, 1.791 mmol) in 15 mL of THF, were added stepwise triethylamine (0.67 mL, 4.836 mmol) and pivaloyl chloride (0.24 mL, 1.971 mmol). The reaction mixture was stirred at −10° C. for 1 h and then LiCl (0.084 g, 1.971 mmol) and (R)-4-benzyloxazolidin-2-one (0.349 g, 1.971 mmol) were added stepwise. After warming slowly to room temperature and stirring overnight, the reaction mixture was diluted with ethyl acetate (80 mL) and washed with saturated NaHCO₃ solution and brine. The organic layer was dried (Na₂SO₄), filtered, and concentrated under reduced pressure. The product was isolated by Flash column chromatography (silica gel column) eluting with 0-100% dichloromethane/hexanes to give the title compound as colorless oil (0.666 g, 90% yield). GC-MS: $t_R$=9.6 min; m/z 411 (M⁺).

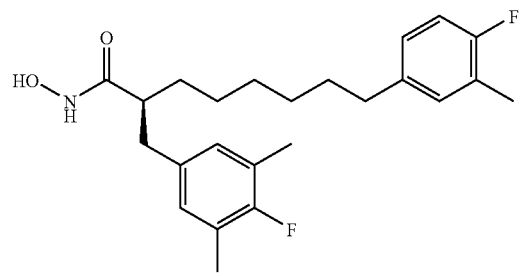

(S)-2-(4-Fluoro-3,5-dimethyl-benzyl)-8-(4-fluoro-3-methyl-phenyl)-octanoic acid hydroxyamide (Compound 168124)

To a solution of (R)-4-Benzyl-3-[(S)-2-(4-fluoro-3,5-dimethyl-benzyl)-8-(4-fluoro-3-methyl-phenyl)-octanoyl]-oxazolidin-2-one (0.036 g, 0.0657 mmol) in 2.5 mL of THF/MeOH/50% NH₂OH—H₂O (2:2:1), was added KCN (0.001 g, 0.007 mmol). After stirring at room temperature for overnight, the reaction mixture was acidified with concentrated HCl to pH=2 and filtered. The product was isolated by RP-HPLC eluting with 20-100% acetonitrile (0.025% TFA)/water (0.025% TFA) to give the title compound as an off-white solid (0.005 g, 18% yield). LC-MS: $t_R$=11.1 min, m/z 404 (M+H)⁺; ¹H NMR (300 MHz, CD₃OD) δ 1.21-1.33 (m, 6H), 1.34-1.48 (m, 2H), 1.49-1.66 (m, 2H), 2.18 (s, 6H), 2.21 (s, 3H), 2.23-2.32 (m, 1H), 2.51 (t, J=7.32 Hz, 2H), 2.56-2.62 (m, 1H), 2.67-2.78 (m, 1H), 6.81 (d, J=6.74 Hz, 2H), 6.88 (t, J=9.37 Hz, 1H), 6.91-6.97 (m, 1H), 7.00 (d, J=7.03 Hz, 1H).

Specific Scheme 6

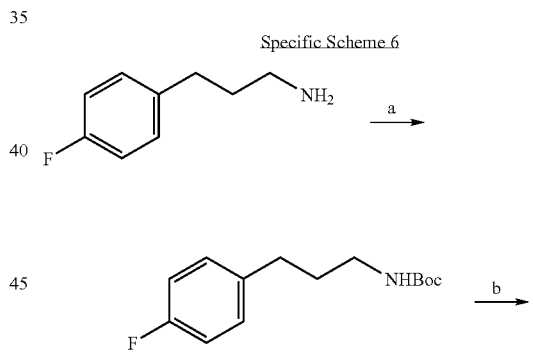

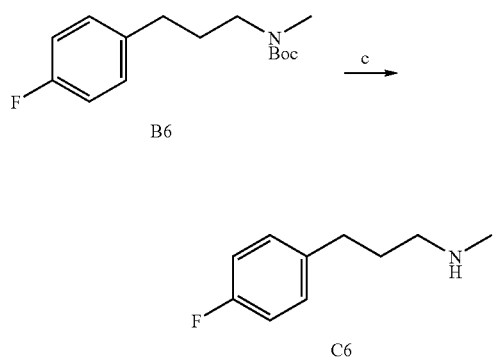

Reagents and conditions: (a) 1.5 eq of Boc₂O, saturated NaHCO₃ solution, dioxane, rt; (b) 1.5 eq of NaH (60% in mineral oil), 2 eq of MeI, THF, rt; (c) TFA/DCM (1:1), rt.

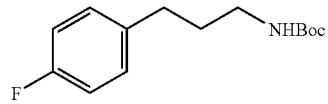

[3-(4-Fluoro-phenyl)-propyl]-carbamic acid tert-butyl ester (A6)

To a solution of 3-(4-fluoro-phenyl)-propylamine (0.300 g, 1.958 mmol) and di-tert-butyl dicarbonate (0.641 g, 2.938 mmol) in 8 mL of dioxane, was added 5 mL of saturated aqueous NaHCO₃ solution. After stirring at room temperature for 64 h, the reaction mixture was diluted with 50 mL of water and extracted with dichloromethane (50 mL×3). The combined organic extracts were dried, filtered. Removal of the solvent under reduced pressure provided the title compound as a white solid (0.525 g, >99% yield), which was used directly in the next step without further purification. GC-MS: $t_R$=8.9 min; m/z 253 (M⁺).

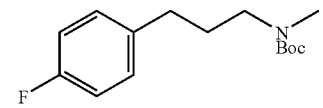

[3-(4-Fluoro-phenyl)-propyl]-methyl-carbamic acid tert-butyl ester (B6)

To a mixture of [3-(4-fluoro-phenyl)-propyl]-carbamic acid tert-butyl ester (0.390 g, 1.540 mmol) and NaH (0.092 g, 2.310 mmol, 60% in mineral oil) in 10 mL of THF, was added via a syringe MeI (0.19 mL, 3.080 mmol). After stirring overnight at room temperature under N₂, the reaction was quenched with NH₄Cl solution (40 mL) and the resulting mixture extracted with dichloromethane (40 mL×3). The combined organic extracts were dried, filtered, and concentrated under reduced pressure. The product was isolated using Flash column chromatography (silica gel) eluting with 0-30% ethyl acetate/hexanes to give the title compound as colorless oil (0.417 g, >99% yield). GC-MS: $t_R$=8.6 min; m/z 267 (M⁺).

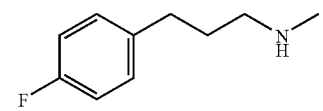

[3-(4-Fluoro-phenyl)-propyl]-methyl-amine (C6)

To a solution of [3-(4-fluoro-phenyl)-propyl]-methyl-carbamic acid tert-butyl ester (0.417 g, 1.560 mmol) in 3 mL of dichloromethane, was added trifluoroacetic acid (3 mL). After stirring at room temperature for 3 h, the reaction mixture was concentrated under reduced pressure. The residue was re-dissolved in 20 mL of ethyl acetate and the resulting solution was washed with NaOH solution (1N) and brine, and dried over anhydrous Na₂SO₄. Removal of the solvent under reduced pressure provided the title compound as a colorless oil (0.189 g, 72% yield), which was used directly in the next step (Step d of Specific Scheme 7) without further purification. GC-MS: $t_R$=5.6 min; m/z 167 (M⁺).

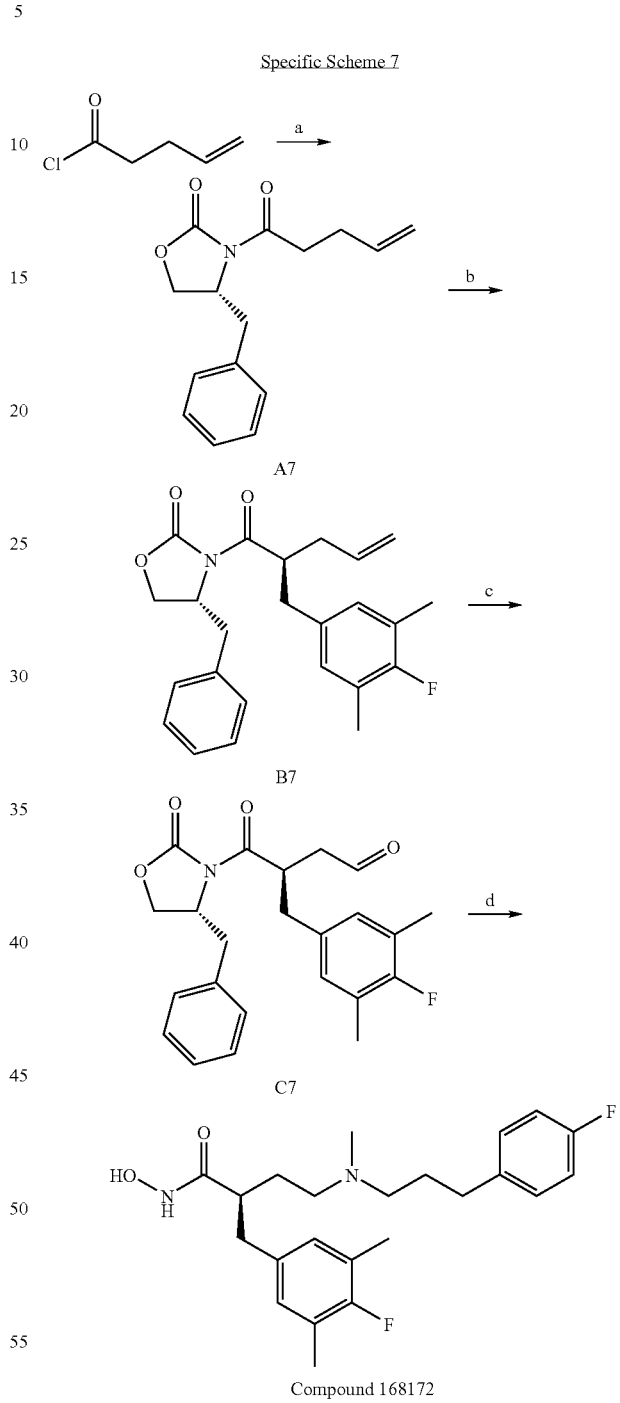

Specific Scheme 7

Reagents and conditions: (a) 1 eq of (R)-4-benzyloxazolidin-2-one, 1.1 eq of n-BuLi (2.5 M in hexane), THF, −78° C. to rt; (b) 1.5 eq of LiHMDS (1.0 M in THF), 1.1 eq of 3,5-dimethyl-4-fluorobenzyl bromide, THF, −78° C. to rt; (c) O₃, 5 eq of Me₂S, DCM, −78° C. to rt; (d) 1.2 eq of [3-(4-fluoro-phenyl)-propyl]-methyl-amine (C6), 1.4 eq of NaBH(OAc)₃, 2 eq of HOAc, dichloroethane, rt; (e) KCN (5 mol %), THF/MeOH/50% NH₂OH—H₂O (2:2:1), rt.

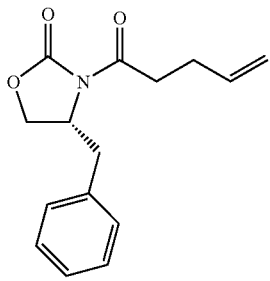

(R)-4-Benzyl-3-pent-4-enoyl-oxazolidin-2-one (A7)

To a cooled (−78° C.) solution of (R)-4-benzyloxazolidin-2-one (2.242 g, 12.652 mmol) in 30 mL of THF, was added n-BuLi (5.6 mL, 13.917 mmol, 2.5 M in hexane). The resulting mixture was stirred at −78° C. under $N_2$ for 15 min and then pent-4-enoyl chloride (1.500 g, 12.652 mmol) was added. After stirring at −78° C. for 1 h the reaction was warmed to room temperature under $N_2$ and stirred overnight. The reaction mixture was quenched with 60 mL of aqueous $NH_4Cl$ solution and extracted with dichloromethane (50 mL×3). The combined organic extracts were dried, filtered, and concentrated under reduced pressure. The product was isolated by Flash column chromatography (silica gel) eluting with 0-30% ethyl acetate/hexanes to give the title compound as colorless oil (2.146 g, 65% yield). GC-MS: $t_R$=4.2 min; m/z 259 (M+).

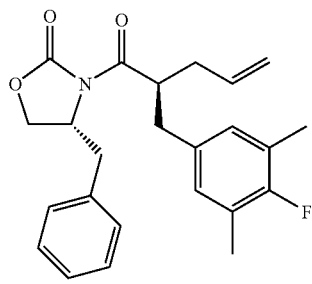

(R)-4-Benzyl-3-[(S)-2-(4-fluoro-3,5-dimethyl-benzyl)-pent-4-enoyl]-oxazolidin-2-one (B7)

To a cooled (−78° C.) solution of (R)-4-benzyl-3-pent-4-enoyl-oxazolidin-2-one (0.500 g, 1.928 mmol) in 15 mL of THF, was added LiHMDS (2.9 mL, 2.9 mmol, 1.0 M in THF). The resulting mixture was stirred at −78° C. under $N_2$ for 1 h and then a solution of 3,5-dimethyl-4-fluorobenzyl bromide (0.460 g, 2.121 mmol) in 5 mL of THF was added. After being stirred at −78° C. for 1 h followed by warming to room temperature over 2 h, the reaction mixture was quenched with 50 mL of aqueous $NH_4Cl$ solution and extracted with dichloromethane (50 mL×3). The combined organic extracts were dried, filtered, and concentrated under reduced pressure. The product was isolated by Flash column chromatography (silica gel) eluting with 0-100% dichloromethane/hexanes to give the title compound as colorless oil (0.221 g, 56% yield). GC-MS: $t_R$=7.0 min; m/z 395 (M+).

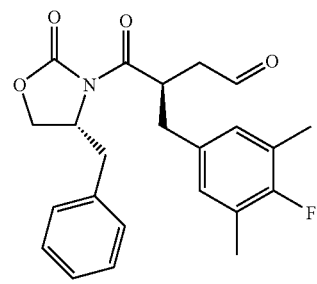

4-((R)-4-Benzyl-2-oxo-oxazolidin-3-yl)-3-((S)-4-fluoro-3,5-dimethyl-benzyl)-4-oxo-butyraldehyde (C7)

A solution of (R)-4-benzyl-3-[(S)-2-(4-fluoro-3,5-dimethyl-benzyl)-pent-4-enoyl]-oxazolidin-2-one (0.220 g, 0.556 mmol) in 10 mL of dichloromethane was cooled to −78° C. and $O_3$ was bubbled through the solution until the color became blue. Then $O_2$ was bubbled through the solution until the blue color disappeared. $Me_2S$ (0.20 mL, 2.723 mmol) was added and after warming to room temperature and stirring overnight, the reaction mixture was concentrated under reduced pressure. The product was isolated by Flash column chromatography (silica gel) eluting with 0-100% dichloromethane/hexanes to give the title compound as colorless oil (0.157 g, 71% yield). GC-MS: $t_R$=7.7 min; m/z 397 (M+).

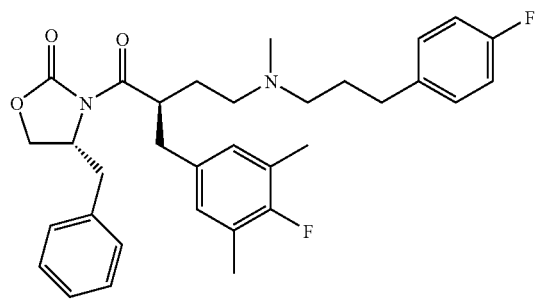

(R)-4-Benzyl-3-((S)-2-(4-fluoro-3,5-dimethyl-benzyl)-4-{[3-(4-fluoro-phenyl)-propyl]-methyl-amino}-butyryl)-oxazolidin-2-one (D7)

To a solution of (R)-4-benzyl-3-[(S)-2-(4-fluoro-3,5-dimethyl-benzyl)-pent-4-enoyl]-oxazolidin-2-one (0.045 g, 0.113 mmol), [3-(4-fluoro-phenyl)-propyl]-methyl-amine (C6, 0.023 g, 0.136 mmol), and acetic acid (0.014 g, 0.226 mmol) in 3 mL of dichloroethane, was added $NaBH(OAc)_3$ (0.034 g, 0.158 mmol). After stirring at room temperature overnight, the reaction was quenched with 20 mL of saturated aqueous $NaHCO_3$ solution and the reaction mixture extracted with ethyl acetate (20 mL×3). The combined organic extracts were dried, filtered, and concentrated under reduced pressure.

The product was isolated by Flash column chromatography (silica gel) eluting with 0-10% methanol/dichloromethane to give the title compound as colorless oil (0.046 g, 75% yield). LC-MS: $t_R$=7.7 min; m/z 549 (M+H)$^+$.

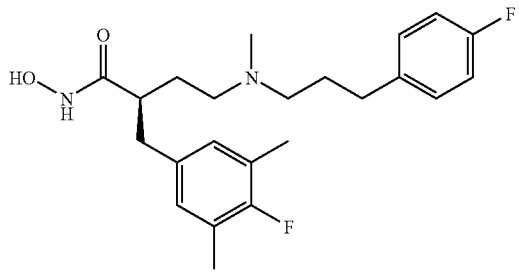

(S)-2-(4-Fluoro-3,5-dimethyl-benzyl)-4-{[3-(4-fluoro-phenyl)-propyl]-methyl-amino}-N-hydroxy-butyramide (Compound 168172

To a solution of (R)-4-benzyl-3-((S)-2-(4-fluoro-3,5-dimethyl-benzyl)-4-{[3-(4-fluoro-phenyl)-propyl]-methyl-amino}-butyryl)-oxazolidin-2-one (0.033 g, 0.0601 mmol) in 2.5 mL of THF/MeOH/50% NH$_2$OH—H$_2$O (2:2:1), was added KCN (0.001 g, 0.006 mmol). After stirring at room temperature overnight, the reaction mixture was acidified with concentrated HCl to pH=2 and filtered. The product was isolated by RP-HPLC eluting with 20-100% acetonitrile (0.025% TFA)/water (0.025% TFA) to give the title compound as an off-white solid (0.016 g, 66% yield). LC-MS: $t_R$=5.5 min, m/z 405 (M+H)$^+$.

Abbreviations:

DMF=dimethylformamide

HOBt=1-hydroxybenzotriazole

NMM=N-methylmorpholine

EDC=N-(-dimethylaminopropyl)-N'-ethylcarbodiimide

DCM=dichloromethane

TFA=trifluoroacetic acid

MS molecular sieves

LiHMDS=Lithium bis(trimethylsilyl)amide

Additional Examples from Table 1

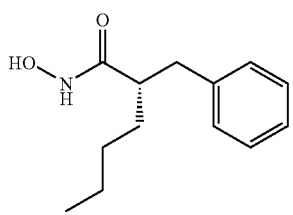

2-Benzyl-hexanoic acid hydroxyamide (Compound 167550) Prepared according to General Scheme 1.
LC-MS: $t_R$=6.3 min, m/z 222 (M+H)$^+$.

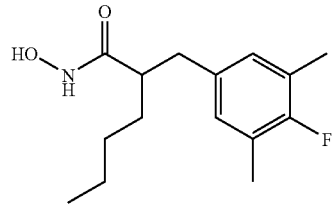

2-(4-Fluoro-3,5-dimethyl-benzyl)-hexanoic acid hydroxyamide (Compound 167533) Prepared according to General Scheme 1.
LC-MS: $t_R$=7.8 min, m/z 268 (M+H)$^+$.

Additional Examples in Table 2

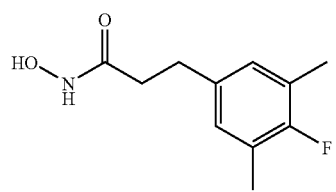

3-(4-Fluoro-3,5-dimethyl-phenyl)-N-hydroxy-propionamide (Compound 167857) Prepared according to General Scheme 2.
LC-MS: $t_R$=5.4 min, m/z 212 (M+H)$^+$.

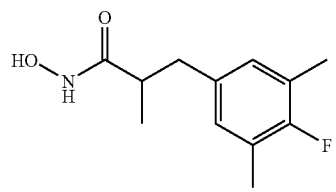

3-(4-Fluoro-3,5-dimethyl-phenyl)-N-hydroxy-2-methyl-propionamide (Compound 167858) Prepared according to General Scheme 2.
LC-MS: $t_R$=5.8 min, m/z 226 (M+H)$^+$.

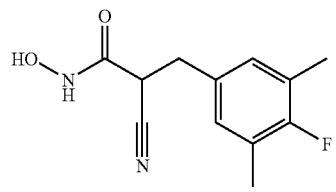

2-Cyano-3-(4-fluoro-3,5-dimethyl-phenyl)-N-hydroxy-propionamide (Compound 167914)) Prepared according to General Scheme 2.
LC-MS: $t_R$=5.4 min, m/z 237 (M+H)$^+$.

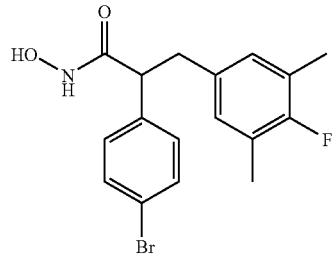

2-(4-Bromo-phenyl)-3-(4-fluoro-3,5-dimethyl-phenyl)-N-hydroxy-propionamide (Compound 167856) Prepared according to General Scheme 3.
LC-MS: $t_R$=8.5 min, m/z 367 (M+H)$^+$.

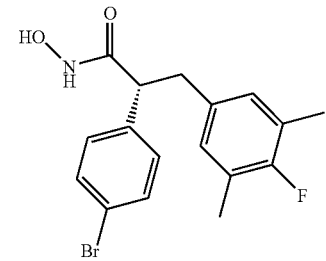

(R)-2-(4-Bromo-phenyl)-3-(4-fluoro-3,5-dimethyl-phenyl)-N-hydroxy-propionamide (Compound 168009) Prepared according to General Scheme 3.
LC-MS: $t_R$=8.4 min, m/z 367 (M+H)$^+$.

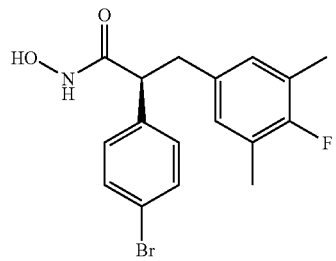

(S)-2-(4-Bromo-phenyl)-3-(4-fluoro-3,5-dimethyl-phenyl)-N-hydroxy-propionamide (Compound 167973) Prepared according to General Scheme 3.
LC-MS: $t_R$=8.4 min, m/z 366/368 (M+H)$^+$.

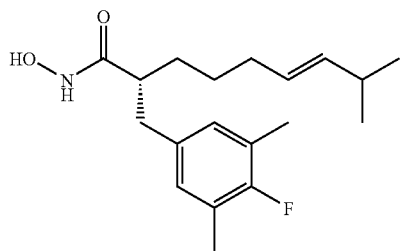

(R)-2-(4-Fluoro-3,5-dimethyl-benzyl)-8-methyl-non-6-enoic acid hydroxyamide (Compound 168051) Prepared according to General Scheme 3
LC-MS: $t_R$=9.8 min, m/z 322 (M+H)$^+$.

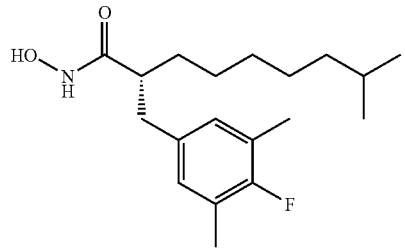

(R)-2-(4-Fluoro-3,5-dimethyl-benzyl)-8-methyl-nonanoic acid hydroxyamide (Compound 168052) Prepared according to General Scheme 3.
LC-MS: $t_R$=10.4 min, m/z 324 (M+H)$^+$.

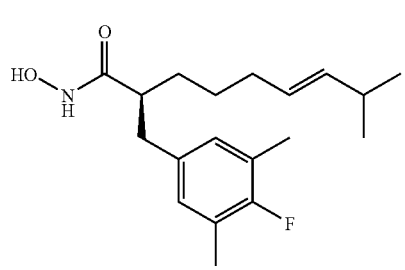

(S)-2-(4-Fluoro-3,5-dimethyl-benzyl)-8-methyl-non-6-enoic acid hydroxyamide (Compound 168023) Prepared according to General Scheme 3.
LC-MS: $t_R$=9.7 min, m/z 322 (M+H)$^+$.

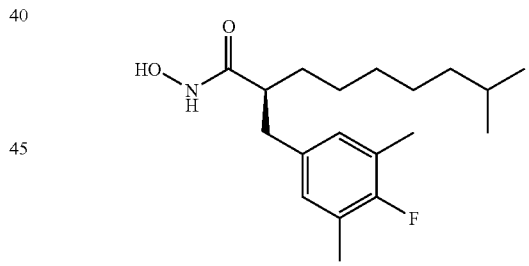

(S)-2-(4-Fluoro-3,5-dimethyl-benzyl)-8-methyl-nonanoic acid hydroxyamide (Compound 168031) Prepared according to General Scheme 3.
LC-MS: $t_R$=10.4 min, m/z 324 (M+H)$^+$.

Additional Examples in Table 3

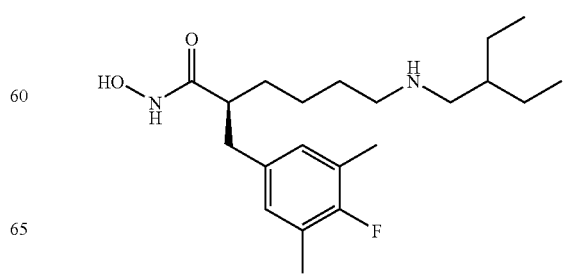

(S)-6-(2-Ethyl-butylamino)-2-(4-fluoro-3,5-dimethyl-benzyl)-hexanoic acid hydroxyamide (Compound 168171) Prepared according to General Scheme 3.
LC-MS: $t_R$=5.3 min, m/z 367 (M+H)$^+$.

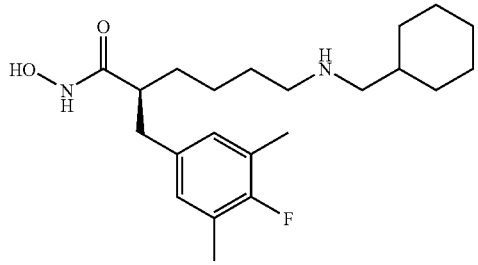

(S)-6-(Cyclohexylmethyl-amino)-2-(4-fluoro-3,5-dimethyl-benzyl)-hexanoic acid hydroxyamide (Compound 168170) Prepared according to General Scheme 3.
LC-MS: $t_R$=5.2 min, m/z 379 (M+H)$^+$.

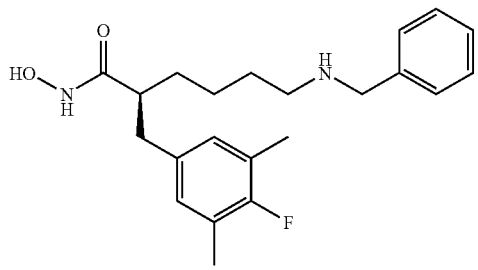

(S)-6-Benzylamino-2-(4-fluoro-3,5-dimethyl-benzyl)-hexanoic acid hydroxyamide (Compound 168149) Prepared according to General Scheme 3.
LC-MS: $t_R$=4.9 min, m/z 373 (M+H)$^+$.

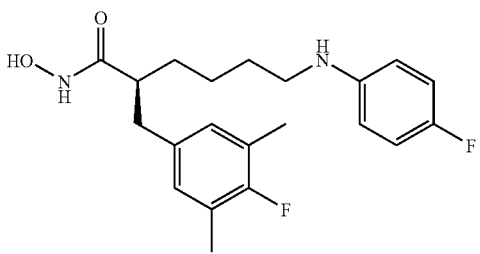

(S)-2-(4-Fluoro-3,5-dimethyl-benzyl)-6-(4-fluoro-phenylamino)-hexanoic acid hydroxyamide (Compound 168132) Prepared according to General Scheme 3.
LC-MS: $t_R$=8.5 min, m/z 362 (M+H)$^+$.

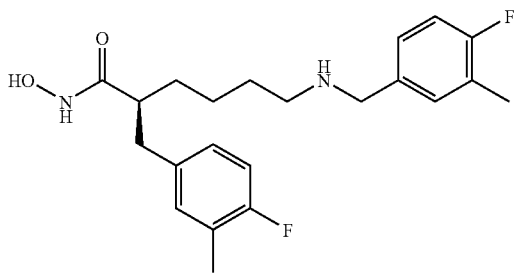

(S)-2-(4-Fluoro-3-methyl-benzyl)-6-(4-fluoro-3-methyl-benzylamino)-hexanoic acid hydroxyamide (Compound 168139) Prepared according to General Scheme 3.
LC-MS: $t_R$=4.8 min, m/z 391 (M+H)$^+$.

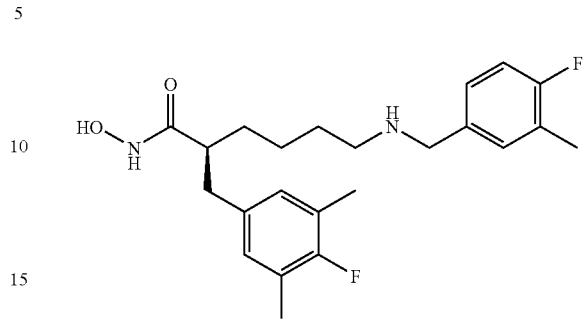

(S)-2-(4-Fluoro-3,5-dimethyl-benzyl)-6-(4-fluoro-3-methyl-benzylamino)-hexanoic acid hydroxyamide (Compound 168050) Prepared according to General Scheme 3.
LC-MS: $t_R$=5.1 min, m/z 405 (M+H)$^+$.

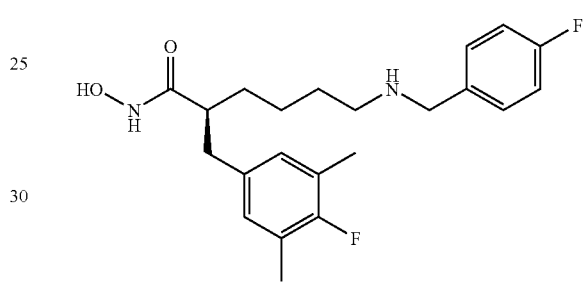

(S)-6-(4-Fluoro-benzylamino)-2-(4-fluoro-3,5-dimethyl-benzyl)-hexanoic acid hydroxyamide (Compound 168117). Prepared according to General Scheme 3.
LC-MS: $t_R$=4.8 min, m/z 391 (M+H)$^+$.

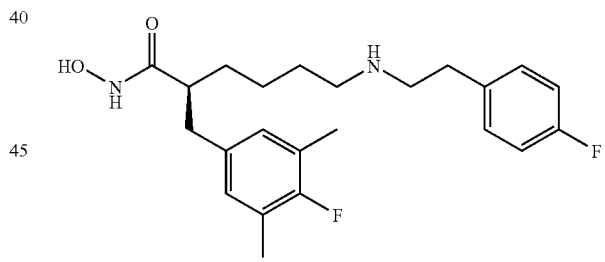

(S)-2-(4-Fluoro-3,5-dimethyl-benzyl)-6-[2-(4-fluoro-phenyl)-ethylamino]-hexanoic acid hydroxyamide (Compound 168122) Prepared according to General Scheme 3.
LC-MS: $t_R$=5.3 min, m/z 405 (M+H)$^+$.

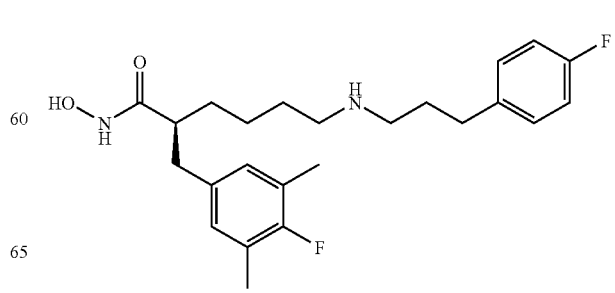

(S)-2-(4-Fluoro-3,5-dimethyl-benzyl)-6-[3-(4-fluoro-phenyl)-propylamino]-hexanoic acid hydroxyamide (Compound 168123) Prepared according to General Scheme 3.
LC-MS: $t_R$=5.5 min, m/z 419 (M+H)$^+$.

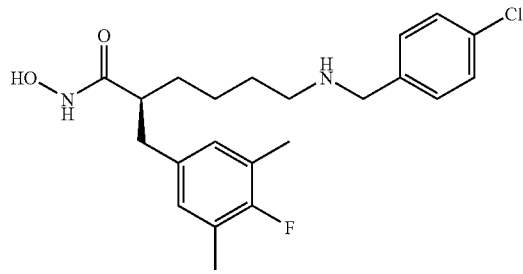

(S)-6-(4-Chloro-benzylamino)-2-(4-fluoro-3,5-dimethyl-benzyl)-hexanoic acid hydroxyamide (Compound 168125) Prepared according to General Scheme 3.
LC-MS: $t_R$=6.0 min, m/z 407/409 (M+H)$^+$.

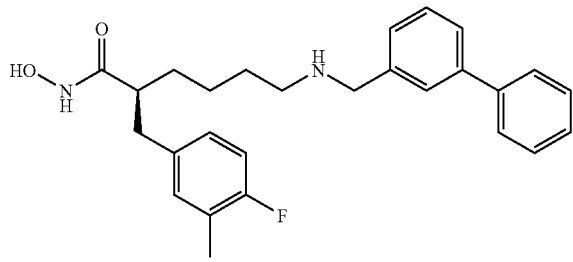

(S)-6-[(Biphenyl-3-ylmethyl)-amino]-2-(4-fluoro-3-methyl-benzyl)-hexanoic acid hydroxyamide (Compound 168140) Prepared according to General Scheme 3.
LC-MS: $t_R$=5.7 min, m/z 435 (M+H)$^+$.

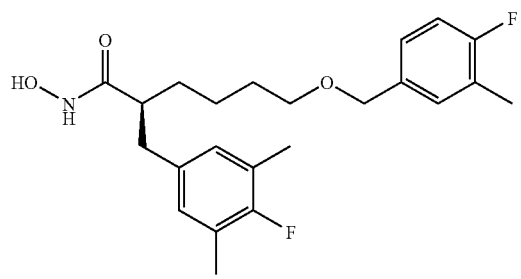

(S)-2-(4-Fluoro-3,5-dimethyl-benzyl)-6-(4-fluoro-3-methyl-benzyloxy)-hexanoic acid hydroxyamide (Compound 168141) Prepared according to General Scheme 4.
LC-MS: $t_R$=9.6 min, m/z 406 (M+H)$^+$.

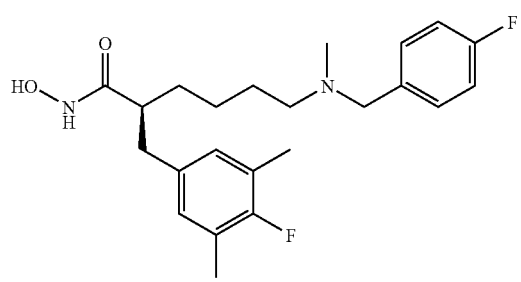

(S)-6-[(4-Fluoro-benzyl)-methyl-amino]-2-(4-fluoro-3,5-dimethyl-benzyl)-hexanoic acid hydroxyamide (Compound 168126) Prepared according to General Scheme 3.
LC-MS: $t_R$=5.7 min, m/z 405 (M+H)$^+$.

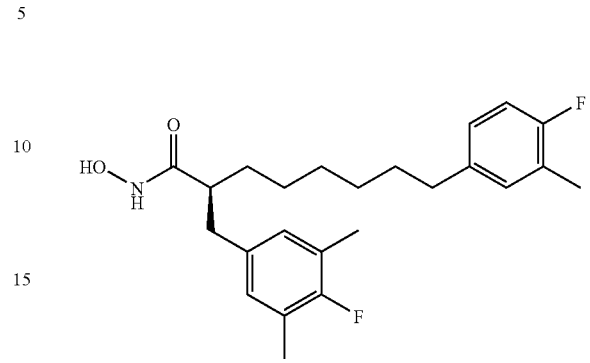

(S)-2-(4-Fluoro-3,5-dimethyl-benzyl)-8-(4-fluoro-3-methyl-phenyl)-octanoic acid hydroxyamide (Compound 168124) Prepared according to General Scheme 5.
LC-MS: $t_R$=11.1 min, m/z 404 (M+H)$^+$.

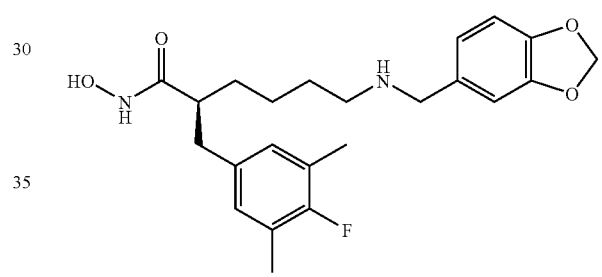

(S)-6-[(Benzo[1,3]dioxol-5-ylmethyl)-amino]-2-(4-fluoro-3,5-dimethyl-benzyl)-hexanoic acid hydroxyamide (Compound 168148) Prepared according to General Scheme 3.
LC-MS: $t_R$=5.0 min, m/z 417 (M+H)$^+$.

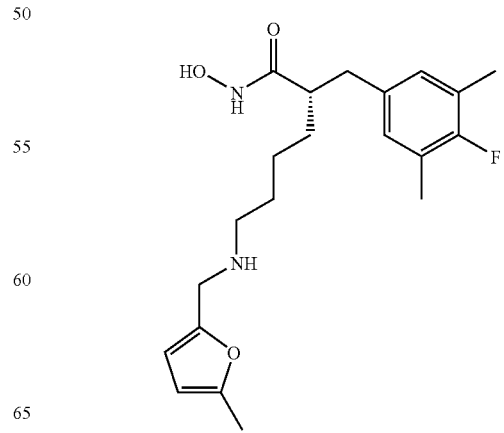

(S)-2-(4-Fluoro-3,5-dimethyl-benzyl)-6-[(5-methyl-furan-2-ylmethyl)-amino]-hexanoic acid hydroxyamide (Compound 168157) Prepared according to General Scheme 3.
LC-MS: $t_R$=4.9 min, m/z 377 (M+H)$^+$.

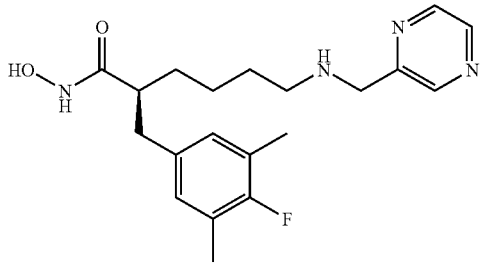

(S)-2-(4-Fluoro-3,5-dimethyl-benzyl)-6-[(pyrazin-2-ylmethyl)-amino]-hexanoic acid hydroxyamide (Compound 168179) Prepared according to General Scheme 3.
LC-MS: $t_R$=4.1 min, m/z 375 (M+H)$^+$.

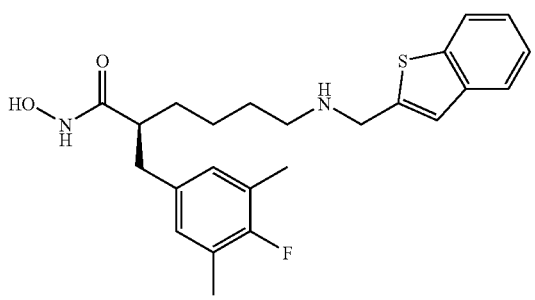

(S)-6-[(Benzo[b]thiophen-2-ylmethyl)-amino]-2-(4-fluoro-3,5-dimethyl-benzyl)-hexanoic acid hydroxyamide (Compound 168180) Prepared according to General Scheme 3.
LC-MS: $t_R$=5.5 min, m/z 429 (M+H)$^+$.

Additional Examples in Table 4

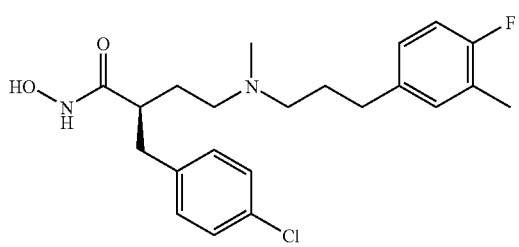

2R-(4-Chloro-benzyl)-4-{[3-(4-fluoro-3-methyl-phenyl)-propyl]-methyl-amino}-N-hydroxy-butyramide (Compound 168150) Prepared according to General Scheme 3.
LC/MS: $t_R$=5.3 min. MS (API-ES) m/z 407 (M+H$^+$)

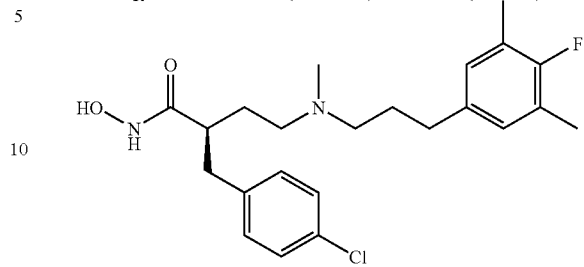

2R-(4-Chloro-benzyl)-4-{[3-(4-fluoro-3,5-dimethyl-phenyl)-propyl]-methyl-amino}-N-hydroxy-butyramide (Compound 168156) Prepared according to General Scheme 3.
LC/MS: $t_R$=5.7 min. MS (API-ES) m/z 421 (M+H$^+$)

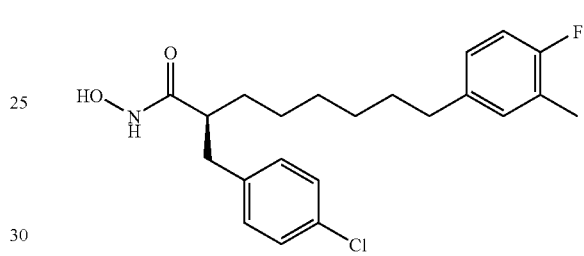

(S)-2-(4-Chloro-benzyl)-8-(4-fluoro-3-methyl-phenyl)-octanoic acid hydroxyamide (Compound 168134) Prepared according to General Scheme 5.
LC-MS: $t_R$=10.5 min, m/z 392/394 (M+H)$^+$.

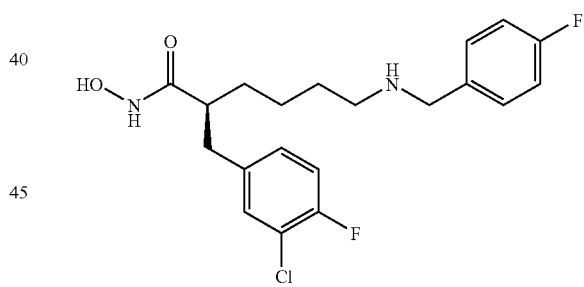

(S)-2-(3-Chloro-4-fluoro-benzyl)-6-(4-fluoro-benzylamino)-hexanoic acid hydroxyamide (Compound 168164) Prepared according to General Scheme 3.
LC-MS: $t_R$=4.8 min, m/z 397 (M+H)$^+$.

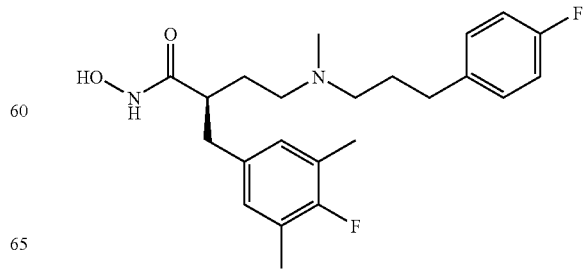

(S)-2(4-Fluoro-3,5-dimethyl-benzyl)-4 {[3-(4-fluoro-phenyl)-propyl]-methyl-amino}N-hyoxy-butyramide (Compound 168172) Prepared according to General Scheme 3. LC-MS: $t_R$=5.5 min, m/z 405 (M+H)$^+$.

What is claimed is:

1. A compound of the formula

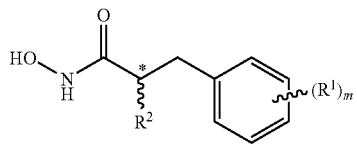

where $R^1$ is F, Cl, alkyl of 1-3 carbons;

m is an integer having the value of 1 to 3;

$R^2$ is alkyl of 1-9 carbons; $C_1$-$C_6$ alkylphenyl where phenyl is substituted with 0-3 $R^1$ groups, $C_1$-$C_6$ alkylcyclohexyl, $(CH_2)_nOR^3$, $(CH_2)_nNHR^4$, $(CH_2)_nCF_3$, $CH_2OCH_2$phenyl; $(CH_2)_nNH(CH_2)_nR^4$, $(CH_2)_nNR^6R^4$, $(CH_2)_nNR^6(CH_2)_nR^4$, $(CH_2)_nO(CH_2)_nR^4$, $(CH_2)_nOR^4$, CN, phenyl substituted with 0 to 3 $R^1$ groups, an alkenyl group having 2 to 9 carbons and one double bond, n is an integer having the value of 1 to 8;

$R^3$ is H, alkyl of 1 to 6 carbons, alkylphenyl where the alkylgroup has 1 to 6 carbons and the phenyl is substituted with 0-3 $R^1$ groups;

$R^4$ is H, alkyl of 1 to 10 carbons, $(CH_2)_p$cyclohexyl, C(O)alkyl of 1 to 4 carbons, C(O)alkylphenyl where the alkylgroup has 1 to 4 carbons and the phenyl is substituted with 0-3 $R^1$ groups or with a 5 to 6 membered heteroayl group having 1 to 2 heteroatoms selected from O, S, and N, or with a 5 to 6 membered heteroaryl group having 1 to 2 heteroatoms selected from O, S and N and condensed with a phenylgroup, said heteroaryl or condensed heteroaryl group itself substituted with 0-3 $R^1$ groups, or $R^4$ is $C(O)(CH_2)_pCOOH$, $(CH_2)_p$phenyl where the phenyl is substituted with 0-3 $R^1$ groups or with a $NO_2$ group, or $R^4$ is $C(O)OC_1$-$C_6$alkyl, or $R^4$ is $CH(CH_3)$phenyl where the phenyl is substituted with 0-3 $R^1$ groups, or $R^4$ is $C(O)(CH_2)_p$phenyl where the phenyl is substituted with 0-3 $R^1$ groups, or $R^4$ is C(O)CH(Ph)$_2$, C(O)—CH$_2$-(3PhO—)Ph, or $R^4$ is a 5 to 6 membered heteroaryl group having 1 to 2 heteroatoms selected from O, S, and N, or a 5 to 6 membered heteroaryl group having 1 to 2 heteroatoms selected from O, S and N and condensed with a phenylgroup, said heteroaryl or condensed heteroaryl group itself substituted with 0-3 $R^1$ groups, or $R^4$ is CH$_2$heteroaryl ** CH$_2$heteroaryl condensed with phenyl where the heteroaryl group is 5 or 6 membered and has 1 to 2 heteroatoms selected from O, S said heteroaryl group or condensed heteroaryl itself substituted with 0-3 $R^1$ groups, or $R^4$ is $SO_2$-alkyl of 1 to 6 carbons, $SO_2$-Ph where the phenyl is substituted with 0-3 $R^1$ groups or with $NO_2$ or with $COOR^5$ group, or $R^4$ is C(O)NH-alkylphenyl, or C(O)NH-phenyl where the alkyl group has 1 to 4 carbons and where the phenyl is substituted with 0-3 $R^1$ groups;

p is an integer having the value of 0 to 4;

$R^5$ is alkyl of 1 to 6 carbons or phenyl substituted with 0-3 $R^1$ groups or with an OPh group;

$R^6$ is alkyl of 1 to 6 carbons;

the asterisk indicates an asymmetric carbon, the wavy line represents a bond that can be in the R or in the S configuration, or a pharmaceutically acceptable salt of said compound, with the proviso that compounds selected from the group consisting of compounds identified below with structural formulas

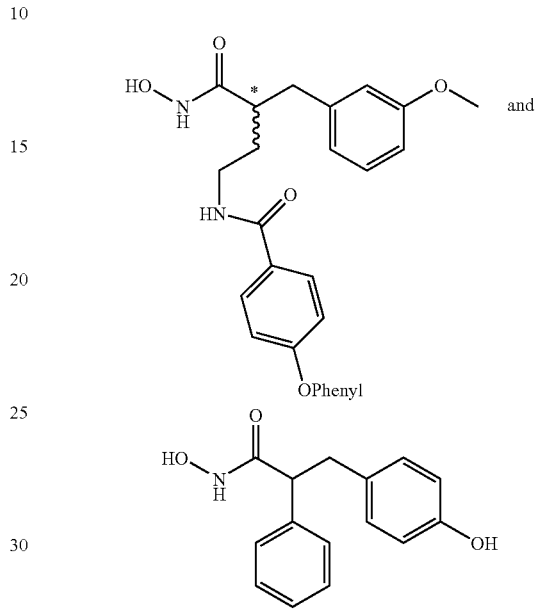

are not included in the claim.

2. A compound in accordance with claim 1 where $R^1$ is selected independently from the group consisting of F, Cl, methyl.

3. A compound in accordance with claim 2 where m is an integer having the value of 2 or 3.

4. A compound in accordance with claim 3 where m is 2, one $R^1$ group is methyl in the 3 (meta) position on the phenyl ring, and the other $R^1$ group is fluoro in the 4 (para) position of the phenyl ring.

5. A compound in accordance with claim 2 where m is 3, two $R^1$ groups are methyl in the 3,3 (meta, meta) positions on the phenyl ring and the third $R^1$ group is fluoro in the 4 (para) position of the phenyl ring.

6. A compound of the formula

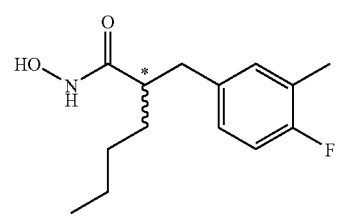

where the asterisk represents that the adjacent carbon is asymmetric and the wavy line represents a bond which can be of either R or S configuration, or a pharmaceutically acceptable salt of said compound.

7. A compound of the formula

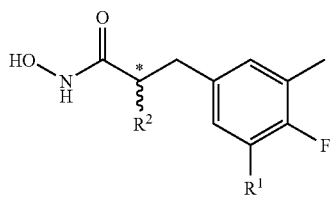

where

R$^1$ is H or alkyl of 1 to 6 carbons;

R$^2$ is H, CN, 4-Br-phenyl, alkyl of 1 to 8 carbons, alkenyl where the alkenyl group has 2 to 8 carbons and one double bond, (CH$_2$)$_4$—O—CH$_2$-3Me-4F-phenyl or (CH$_2$)$_{6-4}$F-phenyl, the asterisk represents that the adjacent carbon can be asymmetric and the wavy line represents a bond which can be of either R or S configuration, or a pharmaceutically acceptable salt of said compound.

8. A compound in accordance with claim 7 where R$^1$ is H or methyl.

9. A compound in accordance with claim 8 where R$^2$ is H or methyl.

10. A compound in accordance with claim 8 where R$^2$ is 4-Br-phenyl, (CH$_2$)$_4$—O—CH$_2$-3Me-4F-phenyl or (CH$_2$)$_{6-4}$F-phenyl.

11. A compound in accordance with claim 8 where R$^2$ is alkenyl.

12. A compound of the formula

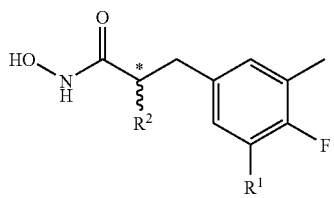

where

R$^1$ is H or alkyl of 1 to 6 carbons;

R$^2$ is (CH$_2$)$_n$NR$^6$(CH$_2$)$_p$-phenyl, (CH$_2$)$_n$NH(CH$_2$)$_p$phenyl said phenyl groups being substituted with 0 to 3 groups selected from the group F, Cl and methyl, (CH$_2$)$_n$NH (CH$_2$)$_p$cyclohexyl, (CH$_2$)$_n$NH(CH$_2$)$_p$furanyl, (CH$_2$)$_n$ NH(CH$_2$)$_p$pyrazinyl, (CH$_2$)$_n$NH(CH$_2$)$_p$-2-benzo[b] thienyl said furanyl, pyrazinyl and 2-benzo[b]thienyl rings being substituted with 0 to 3 R$^1$ groups n is an integer having the value of 1 to 6, p is an integer having the value of 0 to 4, R$^6$ is alkyl of 1 to 3 carbons, the asterisk represents that the adjacent carbon can be asymmetric and the wavy line represents a bond which can be of either R or S configuration, or a pharmaceutically acceptable salt of said compound.

13. A compound in accordance with claim 12 where R$^1$ is H or methyl.

14. A compound in accordance with claim 13 where n is 4 and p is 1.

15. A compound in accordance with claim 13 where n is 4 and R$^6$ is methyl.

16. A compound selected from the group of compounds consisting of

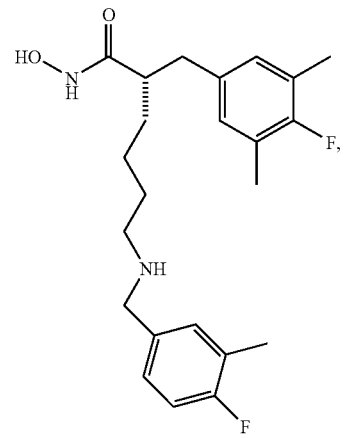

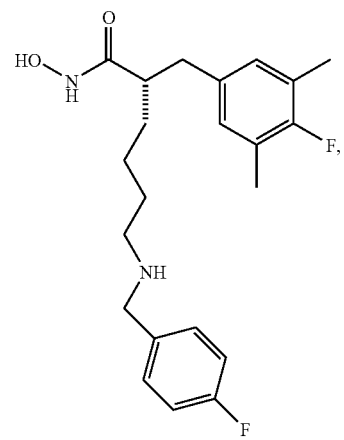

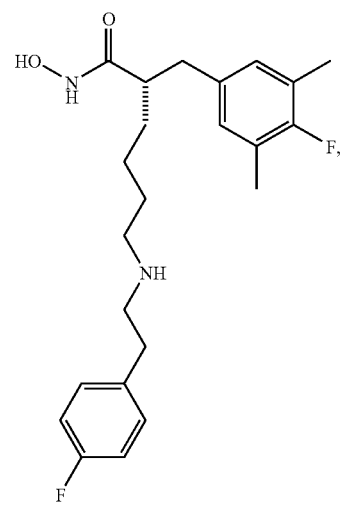

-continued
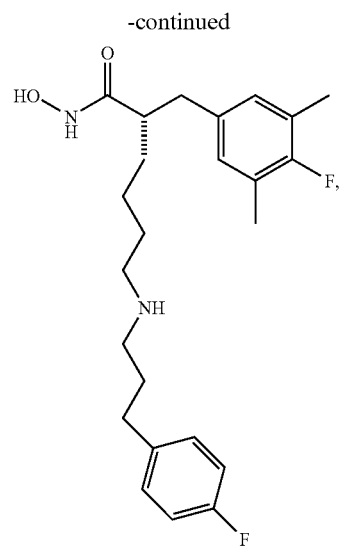
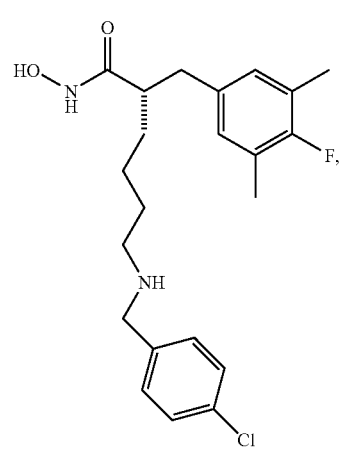
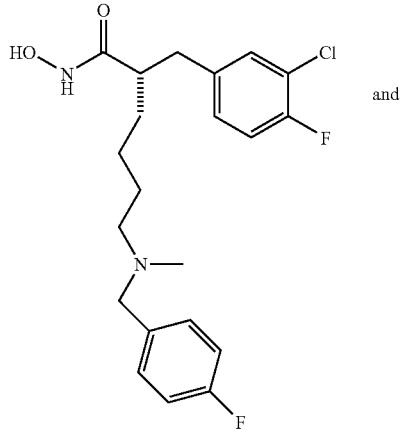
and
-continued
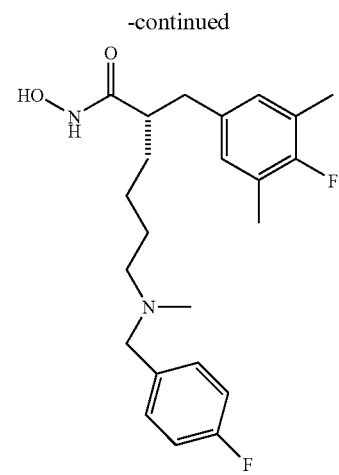
or a pharmaceutically acceptable salt of said compound.
17. A compound of the formula
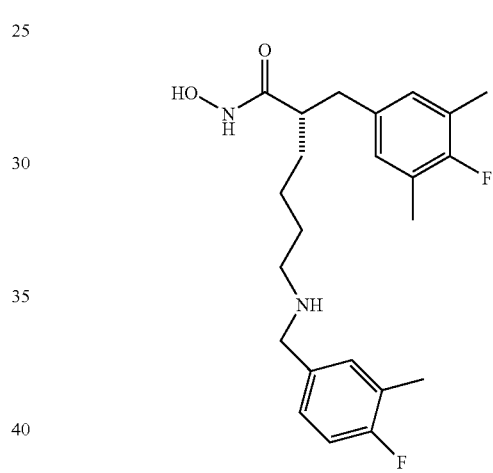
or a pharmaceutically acceptable salt of said compound.
18. A compound of the formula
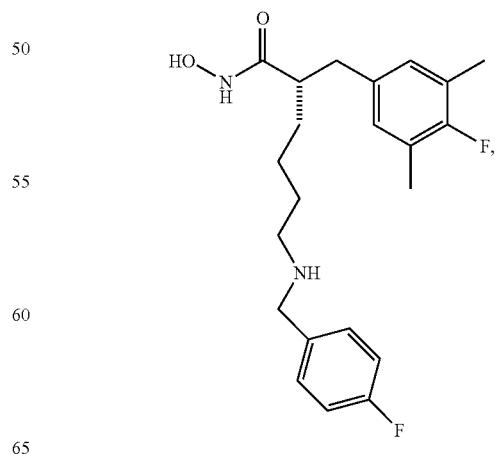
or a pharmaceutically acceptable salt of said compound.

19. A pharmaceutical composition containing a pharmaceutically acceptable excipient and one or more compounds of the formula

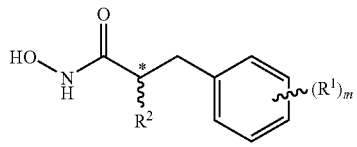

where
R$^1$ is F, Cl, alkyl of 1-3 carbons;
m is an integer having the value of 1 to 3;
R$^2$ is alkyl of 1-9 carbons; C$_1$-C$_6$ alkylphenyl where phenyl is substituted with 0-3 R$^1$ groups, C$_1$-C$_6$ alkylcyclohexyl, (CH$_2$)$_n$OR$^3$, (CH$_2$)$_n$NHR$^4$, (CH$_2$)$_n$CF$_3$, CH$_2$OCH$_2$phenyl; (CH$_2$)$_n$NH(CH$_2$)$_n$R$^4$, (CH$_2$)$_n$NR$^6$R$^4$, (CH$_2$)$_n$NR$^6$(CH$_2$)$_n$R$^4$, (CH$_2$)$_n$O(CH$_2$)$_n$R$^4$, (CH$_2$)$_n$OR$^4$, CN, phenyl substituted with 0 to 3 R$^1$ groups, an alkenyl group having 2 to 9 carbons and one double bond,
n is an integer having the value of 1 to 8;
R$^3$ is H, alkyl of 1 to 6 carbons, alkylphenyl where the alkylgroup has 1 to 6 carbons and the phenyl is substituted with 0-3 R$^1$ groups;
R$^4$ is H, alkyl of 1 to 10 carbons, (CH$_2$)$_p$cyclohexyl, C(O)alkyl of 1 to 4 carbons, C(O)alkylphenyl where the alkylgroup has 1 to 4 carbons and the phenyl is substituted with 0-3 R$^1$ groups or with a 5 to 6 membered heteroaryl group having 1 to 2 heteroatoms selected from O, S, and N, or with a 5 to 6 membered heteroaryl group having 1 to 2 heteroatoms selected from O, S and N and condensed with a phenylgroup, said heteroaryl or condensed heteroaryl group itself substituted with 0-3 R$^1$ groups, or R$^4$ is C(O)(CH$_2$)$_p$COOH, (CH$_2$)$_p$phenyl where the phenyl is substituted with 0-3 R$^1$ groups or with a NO$_2$ group, or R$^4$ is C(O)OC$_1$-C$_6$alkyl, or R$^4$ is CH(CH$_3$)phenyl where the phenyl is substituted with 0-3 R$^1$ groups, or R$^4$ is C(O)(CH$_2$)$_p$phenyl where the phenyl is substituted with 0-3 R$^1$ groups, or R$^4$ is C(O)CH(Ph)$_2$, C(O)—CH$_2$-(3PhO—)Ph, or R$^4$ is a 5 to 6 membered heteroaryl group having 1 to 2 heteroatoms selected from O, S, and N, or a 5 to 6 membered heteroaryl group having 1 to 2 heteroatoms selected from O, S and N and condensed with a phenylgroup, said heteroaryl or condensed heteroaryl group itself substituted with 0-3 R$^1$ groups, or R$^4$ is CH$_2$heteroaryl ** CH$_2$heteroaryl condensed with phenyl where the heteroaryl group is 5 or 6 membered and has 1 to 2 heteroatoms selected from O, S said heteroaryl group or condensed heteroaryl itself substituted with 0-3 R$^1$ groups, or R$^4$ is SO$_2$-alkyl of 1 to 6 carbons, SO$_2$-Ph where the phenyl is substituted with 0-3 R$^1$ groups or with NO$_2$ or with COOR$^5$ group, or R$^4$ is C(O)NH-alkylphenyl, or C(O)NH-phenyl where the alkyl group has 1 to 4 carbons and where the phenyl is substituted with 0-3 R$^1$ groups;
p is an integer having the value of 0 to 4;
R$^5$ is alkyl of 1 to 6 carbons or phenyl substituted with 0-3 R$^1$ groups or with an OPh group;
R$^6$ is alkyl of 1 to 6 carbons;
the asterisk indicates an asymmetric carbon, the wavy line represents a bond that can be in the R or in the S configuration, or a pharmaceutically acceptable salt of said compound.

* * * * *

UNITED STATES PATENT AND TRADEMARK OFFICE
CERTIFICATE OF CORRECTION

PATENT NO. : 7,807,720 B2
APPLICATION NO. : 12/011888
DATED : October 5, 2010
INVENTOR(S) : Johnson et al.

It is certified that error appears in the above-identified patent and that said Letters Patent is hereby corrected as shown below:

In column 2 (page 1 item 56) at line 13, Under Other Publications, change "Additins" to --Additions--.

In column 2 (page 1 item 56) at line 16, Under Other Publications, change "Versitle" to --Versatile--.

In column 1 at line 58, Change "Biopphys." to --Biophys.--.

In column 1 at line 64, Change "bacillus anthraci" to --bacillus anthracis--.

In column 3 at line 11, Change "heteroayl" to --heteroaryl--.

In column 4 at line 38, After "MAP kinase" delete "kinase".

In column 9-10 at line 67 (col. 9), at line 61 (col. 10), Change "bemzylbromide" to --benzylbromide--.

In column 19 at line 52, Change "$R_3$" to --$R^3$--.

In column 19 at line 55, Change "R" to --$R^4$--.

In column 23 at line 10, Change "methanol/dichoromethane" to --methanol/dichloromethane--.

In column 24 at line 67, After "175.31" insert --.--.

In column 32 at line 49, Change "tritited" to --tritiated--.

In column 42 at line 3, After "Scheme 3" insert --.--.

In column 48 at line 4, After "(M+H$^+$)" insert --.--.

In column 48 at line 20, After "(M+H$^+$)" insert --.--.

Signed and Sealed this
Tenth Day of May, 2011

David J. Kappos
*Director of the United States Patent and Trademark Office*

CERTIFICATE OF CORRECTION (continued)
U.S. Pat. No. 7,807,720 B2

In column 49 at line 2, Change "N-hyoxy" to --N-hydroxy--.

In column 39 at line 36, In Claim 1, change "heteroayl" to --heteroaryl--.

In column 55 at line 30, In Claim 19, change "heteroayl" to --heteroaryl--.